(12) United States Patent
Ismagilov et al.

(10) Patent No.: US 8,622,987 B2
(45) Date of Patent: Jan. 7, 2014

(54) CHEMISTRODE, A PLUG-BASED MICROFLUIDIC DEVICE AND METHOD FOR STIMULATION AND SAMPLING WITH HIGH TEMPORAL, SPATIAL, AND CHEMICAL RESOLUTION

(75) Inventors: Rustem F. Ismagilov, Chicago, IL (US); Delai Chen, Cambridge, MA (US); Weishan Liu, Chicago, IL (US); Wenbin Du, Chicago, IL (US)

(73) Assignee: The University of Chicago, Chicago, IL (US)

( * ) Notice: Subject to any disclaimer, the term of this patent is extended or adjusted under 35 U.S.C. 154(b) by 221 days.

(21) Appl. No.: 12/737,058

(22) PCT Filed: Jun. 4, 2009

(86) PCT No.: PCT/US2009/046255
§ 371 (c)(1),
(2), (4) Date: Dec. 22, 2010

(87) PCT Pub. No.: WO2009/149257
PCT Pub. Date: Dec. 10, 2009

(65) Prior Publication Data
US 2011/0112503 A1    May 12, 2011

Related U.S. Application Data

(60) Provisional application No. 61/130,930, filed on Jun. 4, 2008.

(51) Int. Cl.
*A61M 31/00* (2006.01)
(52) U.S. Cl.
USPC .............................. 604/500; 600/573; 436/34

(58) Field of Classification Search
USPC .......................................... 604/500; 600/573
See application file for complete search history.

(56) References Cited

U.S. PATENT DOCUMENTS

| 4,853,336 A | 8/1989 | Saros et al. |
| 4,963,498 A | 10/1990 | Hillman et al. |

(Continued)

FOREIGN PATENT DOCUMENTS

| CN | 2482070 | 3/2002 |
| EP | 0 816 837 | 1/1998 |

(Continued)

OTHER PUBLICATIONS

Tanaka, H. et al., "*Ethanol Production from Starch by a Coimmobilized Mixed Culture System of Aspergillus awamori and Zymomonas mobilis*", Biotechnology and Bioengineering, vol. XXVII, 1986, pp. 1761-1768.

(Continued)

*Primary Examiner* — Max Hindenburg
*Assistant Examiner* — Renee Danega
(74) *Attorney, Agent, or Firm* — Brinks Gilson & Lione

(57) ABSTRACT

A method for sampling and/or introducing a matter to an environment comprises introducing a first array of plugs through a first microchannel of a device into an exchange region of the device in which mass transport between the environment and the plug fluid of at least one plug in the first array of plugs occurs and a second array of plugs is formed. The exchange region is in fluid communication with the first microchannel. The method further comprises directing the second array of plugs into a second microchannel downstream of and in fluid communication with the exchange region.

23 Claims, 7 Drawing Sheets

(56) References Cited

U.S. PATENT DOCUMENTS

| | | | |
|---|---|---|---|
| 5,185,099 A | 2/1993 | Delpuech et al. | |
| 5,191,900 A | 3/1993 | Mishra | |
| 5,739,036 A | 4/1998 | Parris | |
| 5,872,010 A | 2/1999 | Karger et al. | |
| 5,997,636 A | 12/1999 | Gamarnik et al. | 117/70 |
| 6,130,098 A | 10/2000 | Handique et al. | |
| 6,140,053 A | 10/2000 | Köster | 435/6 |
| 6,180,372 B1 | 1/2001 | Franzen | 435/91.1 |
| 6,409,832 B2 | 6/2002 | Weigl et al. | |
| 6,451,610 B1 | 9/2002 | Gorman et al. | |
| 6,524,456 B1 | 2/2003 | Ramsey | |
| 6,561,224 B1 | 5/2003 | Cho | |
| 6,569,631 B1 | 5/2003 | Pantoliano et al. | |
| 7,129,091 B2 | 10/2006 | Ismagilov et al. | |
| 7,294,503 B2 | 11/2007 | Quake et al. | |
| 7,425,310 B2 | 9/2008 | Truex et al. | |
| 2001/0048900 A1 | 12/2001 | Bardell et al. | |
| 2002/0008029 A1 | 1/2002 | Williams et al. | |
| 2002/0012971 A1 | 1/2002 | Mehta | 435/91.2 |
| 2002/0017464 A1 | 2/2002 | Parce et al. | |
| 2002/0022261 A1 | 2/2002 | Anderson et al. | |
| 2002/0058332 A1 | 5/2002 | Quake et al. | |
| 2002/0108096 A1 | 8/2002 | Lee et al. | |
| 2003/0064414 A1 | 4/2003 | Benecky6 et al. | |
| 2003/0116206 A1 | 6/2003 | Hartshorne et al. | |
| 2003/0229376 A1 | 12/2003 | Sandhu | |
| 2004/0005582 A1 | 1/2004 | Shipwash | |
| 2004/0037813 A1 | 2/2004 | Simpson et al. | |
| 2004/0072357 A1 | 4/2004 | Stiene et al. | |
| 2004/0181131 A1 | 9/2004 | Maynard et al. | |
| 2004/0224419 A1 | 11/2004 | Zheng et al. | 436/69 |
| 2005/0087122 A1 | 4/2005 | Ismagilov et al. | |
| 2005/0148091 A1 | 7/2005 | Kitaguchi et al. | |
| 2005/0221339 A1 | 10/2005 | Griffiths et al. | |
| 2005/0272159 A1* | 12/2005 | Ismagilov et al. | 436/34 |
| 2006/0003439 A1 | 1/2006 | Ismagilov et al. | |
| 2006/0073490 A1 | 4/2006 | LeJeune et al. | |
| 2006/0094119 A1 | 5/2006 | Ismagilov et al. | |
| 2007/0003442 A1 | 1/2007 | Link et al. | |
| 2007/0026439 A1 | 2/2007 | Faulstick et al. | |
| 2007/0092914 A1 | 4/2007 | Griffiths et al. | |
| 2007/0172954 A1 | 7/2007 | Ismagilov et al. | |
| 2007/0184489 A1 | 8/2007 | Griffiths et al. | |
| 2007/0195127 A1 | 8/2007 | Ahn et al. | |
| 2008/0115849 A1 | 5/2008 | Yang et al. | |
| 2008/0176263 A1 | 7/2008 | Schultz et al. | |
| 2008/0220422 A1 | 9/2008 | Shoemaker et al. | |
| 2008/0295909 A1 | 12/2008 | Locascio et al. | |
| 2009/0012187 A1 | 1/2009 | Chu et al. | |
| 2009/0021728 A1 | 1/2009 | Heinz et al. | |
| 2009/0060797 A1 | 3/2009 | Mathies et al. | |
| 2009/0068170 A1 | 3/2009 | Weitz et al. | |
| 2009/0197248 A1* | 8/2009 | Griffiths et al. | 435/6 |
| 2010/0022414 A1 | 1/2010 | Link et al. | |

FOREIGN PATENT DOCUMENTS

| | | |
|---|---|---|
| GB | 2097692 A | 11/1982 |
| WO | WO 84/02000 | 5/1984 |
| WO | WO 97/29508 | 8/1997 |
| WO | WO98/02237 | 1/1998 |
| WO | WO 98/52691 | 11/1998 |
| WO | WO 00/21666 | 4/2000 |
| WO | WO 01/77683 A1 | 10/2001 |
| WO | WO 02/12856 A1 | 2/2002 |
| WO | WO 02/23163 A1 | 3/2002 |
| WO | WO 02/25243 A1 | 3/2002 |
| WO | WO 03/042699 A1 | 5/2003 |
| WO | WO 03/044221 A1 | 5/2003 |
| WO | WO 2004/038363 | 5/2004 |
| WO | WO 2007/021343 A2 | 2/2007 |
| WO | WO 2007/030501 A2 | 3/2007 |
| WO | WO 2007/081385 A2 | 7/2007 |
| WO | WO 2007/081386 A2 | 7/2007 |
| WO | WO 2007/081387 A1 | 7/2007 |
| WO | WO 2007/089777 A2 | 8/2007 |
| WO | WO 2007/133710 A2 | 11/2007 |
| WO | WO 2008/021123 A1 | 2/2008 |
| WO | WO 2008/063227 A2 | 5/2008 |
| WO | WO 2008/079274 A1 | 7/2008 |
| WO | WO 2008/130623 A1 | 10/2008 |
| WO | WO 2009/005680 A1 | 1/2009 |
| WO | WO 2009/011808 A1 | 1/2009 |
| WO | WO 2009/015296 A1 | 1/2009 |
| WO | WO 2009/015390 A2 | 1/2009 |
| WO | WO 2009/029229 A2 | 3/2009 |
| WO | WO 2009/037361 A1 | 3/2009 |
| WO | WO 2009/048673 A2 | 4/2009 |
| WO | WO 2009/050512 A2 | 4/2009 |
| WO | WO 2009/061372 A1 | 5/2009 |

OTHER PUBLICATIONS

De-Bashan, L. E. et al., "*Removal of ammonium and phosphorus ions from synthetic wastewater by the microalgae Chlorella vulgaris coimmobilized in alginate beads with the microalgae growth-promoting bacterium Azospirillum brasilense*", Water Research 36 (2002), pp. 2941-2948.

Goodall, J. L. et al., "*Operation of Mixed-Culture Immobilized Cell Reactors for the Metabolism of Meta- and Para-Nitrobenzoate by Comamonas Sp. JS46 and Comamonas Sp. JS47*", Biotechnology and Bioengineering, vol. 59, No. 1, Jul. 5, 1998, pp. 21-27.

He, Mingyan et al., "*Selective Encapsulation of Single Cells and Subcellular Organelles into Picoliter- and Femtoliter-Volume Droplets*", Analytical Chemistry, vol. 77, No. 6, Mar. 15, 2005, pp. 1539-1544.

Huebner, A. et al., "*Quantitative detection of protein expression in single cells using droplet microfluidics*", Chem. Commun, 2007, pp. 1218-1220.

Seong, G.H. et al., "*Fabrication of Microchambers Defined by Photopolymerized Hydrogels and Weirs within Microfluidic Systems: Application to DNA Hybridization*", Analytical Chemistry, vol. 74, No. 14, Jul. 15, 2002, pp. 3372-3377.

Seong G.H. et al., "*Efficient Mixing and reactions within Microfluidic Channels Using Microbead-Supported Catalysts*", J. Am. Chem. Soc. 2002, 124, pp. 13360-13361.

Nisisako, T. et al., "*Formation of Droplets Using Branch Channels in a Microfluidic Circuit*", SICE 2002, Aug. 5-7, 2002, Osaka, pp. 1262-1264.

Chayen, N.E., "*Crystallization with oils: a new dimension in macromolecular crystal growth*", Journal of Crystal Growth 196 (1999), pp. 434-441.

Titomanlio et al., "*Capillary experiments of flow induced crystallization of HDPE*", AlChe Journal, 1990, v36, No. 1, pp. 13-18.

Garcia-Ruiz et al., "*Investigation on protein crystal growth by the gel acupuncture method*", Acta, Cryst., 1994, D50, 99. pp. 484-490.

Sugiura et al., "*Interfacial tension driven monodispersed droplet formation from microfabricated channel array*", Langmuir, 2001, v17, pp. 5562-5566.

Garcia-Ruiz et al. "*A super-saturation wave of protein crystallization*", J. Crystal Growth, 2001, v232, pp. 149-155.

Ng et al., "*Protein crystallization by capillary counter-diffusion for applied crystallographic structure determination*", J. Struct. Biol. 2003, v142, pp. 218-231.

Torkkeli a. et al., "*Droplet Manipulation on a Superhydrophobic Surface for Microchemical Analysis*", 11th International Conference on Solid-State Sensors and Actuators. Digest of Technical Papers, Munich, Jun. 10-14, 2001; vol. 2, pp. 1150-1153.

Roach et al., "*Controlling Nonspecific Protein Adsorption in a Plug-Based Microfluidic System by Controlling Interfacial Chemistry Using Fluorous-Phase Surfactants*", Anal. Chem, vol. 77, No. 2, Feb. 1, 2005, pp. 785-796.

Meier et al., "*Plug-Based Microfluidics with Defined Surface Chemistry to Miniaturize and Control Aggregation of Amyloidogenic Peptides*", Angew. Chem. Int. Ed. 2009, 48, pp. 1487-1489.

Kreutz et al., "*Laterally Mobile, Functionalized Self-Assembled Monolayers at the Fluorous-Aqueous Interface in a Plug-Based*

(56) References Cited

OTHER PUBLICATIONS

*Microfluidic System: characterization and testing with Membrane Protein Crystalization*", Am. Chem. Soc. 2009, 131, pp. 6042-6043.
Holtze et al., "*biocompatible surfactants for water-in-fluorocarbon emulsions*", Lab Chip, 2008, 8, pp. 1632, 1639.
Günther et al., "*Micromixing of Miscible Liquids in Segmented Gas-Liquid Flow*", Langmuir 2005, 21, pp. 1547-1555.
Aota et al., "*Phase separation of gas-liquid and liquid-liquid microflows in microchips*", Microchem Acta, 2009, 164, pp. 249-255.
Chen et al., "*Using Three-Phase Flow of Immiscible Liquids to Prevent coalescence of Droplets in Microfluidic channels: Criteria to Identify the Third Liquid and Validation with Protein Crystallization*" Langmuir 2007, 23 pp. 2255-2260.
Liu et al., "*Isolation, incubation, and parallel functional testing and identification by FISH of rare microbial single-copy cells from multi-species mixtures using the combination of chemistrode and stochastic confinement*", Lab Chip 2009 online DOI: 10.1039/b904958d, pp. 2153-2162.
Adamson et al., "*Production of arrays of chemically distinct nanolitre plugs via repeated splitting in microfluidic devices*", Lab Chip, 2006, 6, pp. 1178-1186.
Boedicker et al., "*Detecting bacteria and determining their susceptibility to antibiotics by stochastic confinement in nanoliter droplets using plug-based microfluidics*", Lab Chip, 2008, 8, pp. 1265-1272.
Li et al., "*Nanoliter Microfluidic Hybrid Method for Simultaneous Screening and Optimization Validated with Crystallization of Membrane Proteins*", Proc. Natl. Acad. Sci. U.S.A. 2006, 103, pp. 19243-19248.
Fidalgo et al., "*Surface-induced droplet fusion in microfluidic devices*", Lab Chip, 2007, 7, pp. 987-986.
Beer et al., "*On-Chip, Real-Time, Single-Copy Polymerase Chain Reaction in Picoliter Droplets*", Anal. Chem., 2007, v. 79, pp. 847-8475.
Burns et al., "*Microfabricated structures for integrated DNA analysis*", Proc. Natl. Acad. Sci. USA, May 1996, vol. 93, pp. 5556-5561.
Pollack et al., "*Electrowetting-based actuation of droplets for integrated microfluidics*", Lab Chip, 2002, v. 2, pp. 96-101.
Vogelstein, et al., "*Digital PCR*", Proc. Natl. Acad. Sci. USA, Aug. 1999, vol. 96, pp. 9236-9241, Genetics.
Zheng et al., "*Formation of Droplets of Alternating Composition in Microfluidic Channels and Applications to Indexing of Concentrations in Droplet-Based Assays*", Anal. Chem., 2004, v. 76, pp. 4977-4982.
Atencia, Javier, et al. "*Controlled Microfluidic Interfaces*", Nature, 2005, vol. 437, No. 29, pp. 648-655.
Gu, Hao et al., "*Droplets Formation and Merging in Two-Phase Flow Microfluidics*", Int. J. Mol. Sci., 2011, vol. 12, pp. 2572-2597.
Shestopalov, Ilya, et al., "*Multi-Step Synthesis of Nanoparticles Performed on Millisecond Time Scale in a Microfluidic Droplet-Based System*", Lab-Chip, 2004, vol. 4, pp. 316-321.
Thorsen, Todd, et al., "*Dynamic Pattern Formation in a Vesicle-Generating Microfluidic Device*", Phys. Rev. Lett., 2001, vol. 86, No. 18, pp. 4163-4166.
Kalinina, Olga, et al., "*Nanoliter Scale PCR with TaqMan Detection*," Nucleic Acids Research, vol. 25, No. 10, (1997), pp. 1999-2004.

\* cited by examiner

CHEMISTRODE, A PLUG-BASED MICROFLUIDIC DEVICE AND METHOD FOR STIMULATION AND SAMPLING WITH HIGH TEMPORAL, SPATIAL, AND CHEMICAL RESOLUTION

This application is the national phase application of PCT Application No. PCT/US2009/046255, filed Jun. 4, 2009, which claims priority to U.S. Provisional patent application Ser. No. 61/130,930, filed Jun. 4, 2008, the entireties of both of which is are hereby incorporated by reference.

The following are hereby incorporated by reference in their entireties for descriptions of uses, applications, and techniques for plug-based methods of analysis, manipulation of plugs, fluid handling, sorting of plugs, device materials, compositions, manufacturing techniques and the use and formation of holding components and loading components:

U.S. Pat. No. 7,129,091 to Rustem F. Ismagilov et al.;
U.S. Provisional Patent Application Ser. No. 60/881,012 to Rustem F. Ismagilov, entitled "Device and Method for Crystallization", filed Jan. 17, 2007;
U.S. Provisional Patent Application Ser. No. 60/875,856 to Delai Chen et al., entitled "Using Three-Phase Flow of Immiscible Liquids to Prevent Coalescence of Droplets in Microfluidic Channels: Criteria to Identify the Third Liquid and Validation with Protein Crystallization", filed Dec. 19, 2006;
U.S. Provisional Patent Application Ser. No. 60/763,574 to Rustem F. Ismagilov et al., entitled "Method and Apparatus for Assaying Blood Clotting", filed Jan. 31, 2006;
U.S. patent application Ser. No. 11/174,298 to Rustem F. Ismagilov et al., entitled "Microfluidic System", filed Jul. 1, 2005;
U.S. patent application Ser. No. 11/082,187 to Rustem F. Ismagilov et al., entitled "Microfluidic System", filed Mar. 16, 2005;
U.S. Provisional Patent Application Ser. No. 60/623,261 to Rustem F. Ismagilov et al., entitled "Microfluidic Devices", filed Oct. 29, 2004;
U.S. Provisional Patent Application Ser. No. 60/585,801 to Rustem F. Ismagilov, entitled "Applications of a Microfluidic System", filed Jul. 2, 2004;
U.S. patent application Ser. No. 10/765,718 to Rustem F. Ismagilov et al., entitled "Device and Method for Pressure-Driven Plug Transport and Reaction", filed Jan. 26, 2004;
U.S. patent application Ser. No. 11/589,700 to Rustem F. Ismagilov et al., entitled "Device and Method for Pressure-Driven Plug Transport and Reaction", filed Oct. 30, 2006;
U.S. Provisional Patent Application Ser. No. 60/394,544 to Rustem F. Ismagilov, entitled "Device and method for pressure-driven plug transport", filed Jul. 8, 2002;
U.S. Provisional Patent Application Ser. No. 60/379,927 to Rustem F. Ismagilov, entitled "Device and Method for Pressure-Driven Plug Transport", filed May 9, 2002;
U.S. Provisional Patent Application Ser. No. 61/080,541 to Timothy R. Kline et al., entitled "Microfluidic Blood Typing And Agglutination Assays", filed Jul. 14, 2008;
International Patent Application Publications WO09015296, WO09037361, WO08079274, WO08063227, WO07133710, WO07081387, WO07081386, WO07081385, WO09048673, WO08021123, WO09061372, WO09050512, WO09029229, WO09011808, WO07030501, WO08130623, WO09005680, and WO09015390; and
U.S. patent application Ser. Nos. 12/127,328, 12/172,186, 11/763,421, 12/058,628, 11/698,298, 11/360,845, 10/963,044, 11/643,151, and 11/633,849.

This invention was made with government support under grant number 0526693 awarded by the National Science Foundation (NSF), grant number EB001903 awarded by the National Institutes of Health, and grant number OD003584 awarded by the National Institutes of Health. The government has certain rights in the invention.

TECHNICAL FIELD

The present disclosure relates to microfluidic devices and methods. More particularly, the present disclosure relates to chemistrodes, plug-based microfluidic devices and methods for stimulation and sampling with high temporal, spatial, and chemical resolution.

BACKGROUND

Microelectrodes have revolutionized the understanding of the spatiotemporal dynamics of systems that generate or respond to electrical signals by enabling localized electrical stimulation and recording. However, such detailed understanding of systems that rely on chemical signals is substantially unavailable.

BRIEF SUMMARY

In one aspect, a method for sampling and/or introducing a matter to an environment comprises introducing a first array of plugs through a first microchannel of a device into an exchange region of the device in which mass exchange between the environment and the plug fluid of at least one plug in the first array of plugs occurs and a second array of plugs is formed. Without wishing to be bound by theory, it is thought that, typically, plugs form at low values of the capillary number. In certain embodiments, as carrier fluid and plug fluid enter into the second channel, the second array of plugs is formed due to the surface tension and immiscibility of the two fluids. The exchange region is in fluid communication with the first microchannel. The method further comprises directing the second array of plugs into a second microchannel downstream of and in fluid communication with the exchange region.

In another aspect, a method for sampling and/or introducing a matter to an environment comprises introducing a first array of plugs through a first microchannel of a device into an exchange region of the device in which mass transport between the environment and at least one plug in the first array of plugs occurs and a second array of plugs forms. The exchange region is in fluid communication with the first microchannel. The method further comprises storing and/or analyzing the contents of at least one plug in the second array of plugs after it passes the exchange region.

In yet another aspect, a method for sampling an aqueous environment comprises introducing a fluid through a first microchannel of a device, wherein the fluid is immiscible with water, into an exchange region of the device in which mass transport between the aqueous environment and the fluid occurs and an array of plugs is formed in the exchange region. The exchange region is in fluid communication with the first microchannel. The method further comprises directing the array of plugs into a second microchannel downstream of and in fluid communication with the exchange region; and storing, analyzing or both storing and analyzing the contents of at least one of the plugs.

In still another aspect, a method for introducing a matter to an environment comprises introducing an array of plugs comprising a carrier fluid and at least one plug, wherein the at least one plug comprises a plug fluid and the matter to be introduced, through a first microchannel of a device into an exchange region of the device in which mass transport from the at least one plug in the array of plugs into the environment occurs, wherein the exchange region is in fluid communication with the first microchannel; directing the carrier fluid into a second microchannel downstream of and in fluid communication with the exchange region, such that the second microchannel is substantially free of plugs; and directing substantially all of the plug fluid of the array of plugs into the environment.

DETAILED DESCRIPTION OF THE PREFERRED EMBODIMENTS

Figure 1:
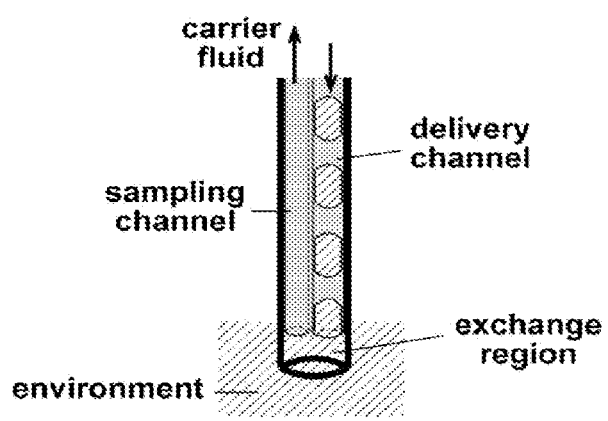
FIG. 1 is an illustrative view of a device for delivering plugs to an exchange region.

Detailed understanding of systems that rely on chemical signals remains out of reach due to the inability to deliver and capture complex chemical information. To address this challenge, the present disclosure provides the "chemistrode." In certain embodiments, the chemistrode is a plug-based microfluidic device that enables stimulation and recording of chemical signals with high spatial and temporal resolution. Like an electrode, the chemistrode does not need to be built into the experimental systems—in certain embodiments, it is brought into contact with a substrate, and, instead of electrical signals, chemical signals are exchanged. In certain embodiments, recording the chemical signal enables offline analysis by multiple, independent analytical methods in parallel, decoupling the stimulating and recording experiment from the equipment and expertise required to identify new molecules and monitor multiple molecular species. When recombined, these analyses provide a time-resolved chemical snapshot of a system's response to stimulation. The physical principles that govern the chemistrode have been characterized and tested to facilitate its application to probing local chemical dynamics of stimulus-responsive matter in chemistry, biology, and materials science.

The microelectrode, voltage clamp, and patch clamp techniques have enabled stimulation and recording of electrical activity with high resolution in both space and time. They revolutionized our understanding of electroactive processes that respond to or generate changes in electric potential, such as redox reactions and currents driven by dynamics of ion channels. Observing and manipulating biological systems with spatial and temporal resolution has been especially successful in systems that are responsive to electric fields. For example, stimulating and recording the responses of neurons with electrodes has transformed neuroscience, and patch-clamp techniques have provided an unprecedented view of the activity of individual ion channels.

However, many biological processes are fundamentally chemical rather than electrical, relying on chemical signals to orchestrate events at the correct time and location. Enormous advances in optical imaging technology combined with new probes and tagging methods have enabled observation of a number of known molecular species involved in chemical signaling processes. In addition, manipulation of known species has been enabled by caging methods that use photo-controllable substrates and other chemical and genetic approaches. However, these technologies may be time consuming to develop and difficult to utilize for multiple or unknown chemical species. Direct sampling, push/pull perfusion, microdialysis, and direct microinjection methods overcome some of these limitations. However, these methods transport chemical pulses by using laminar fluid flow, which broadens the pulses due to Taylor dispersion and result in a loss of temporal resolution and a loss of concentration of the signal. Loss of molecules from solution by adsorption to surfaces of tubes may also occur. As a result, delivering and recording chemical, rather than electrical, signals with high spatial and temporal resolution remains challenging.

Microfluidics is a set of technologies for controlling fluid flow on the micro-scale that was initially developed for microanalytical applications like small-scale DNA sequencing. The inventors have focused on developing microfluidic technology especially suitable for controlling and understanding the dynamics of biological systems in space and time.

In one embodiment, the "chemistrode" is a plug-based microfluidic device for manipulating and observing chemical signals with high spatial and temporal resolution. In certain embodiments, the chemistrode enables methods of concentrating, dialyzing, and characterizing protein samples in plugs on, for example, the microliter, nanoliter or picoliter scale. In certain embodiments, these methods can enable direct sampling of a protein peak from an analytical chromatography column, processing it, and transporting it directly into crystallization trials without losses, dilution, or contamination. This approach is transformative, enabling crystallization of sub-microgram quantities of mammalian proteins.

In one embodiment, the chemistrode comprises a delivery channel configured to deliver carrier fluid, or optionally configured to deliver plugs in the carrier fluid, a sampling or exit channel, configured to remove the carrier fluid, or optionally configured to remove the plugs in the carrier fluid and an exchange region to which delivery and sampling channels are connected. The exchange region is exposed to an environment and enables mass transport between the environment and a plug in the exchange region. In certain embodiments, the exchange region comprises a portion of a microchannel with a hole in the side such that the contents of the microchannel are exposed to the environment. In certain embodiments, the exchange region comprises a T-junction or Y-junction connecting a delivery channel and a sampling or exit channel, and a third channel exposed to the environment. In certain embodiments, the length of the third channel is chosen to be a length long enough to prevent substantial carrier fluid contamination of the environment, but short enough to allow mass transport of at least one analyte from the environment into at least one plug. In certain embodiments comprising a third channel at the exchange region, the third channel should be short enough to allow fast introduction of a reagent to the sample incorporated into the plugs at the exchange region. For example, when sampling blood, anticoagulant may be delivered through plugs in the delivery channel and the third channel should not be so long that blood begins the process of coagulation before mixing with the anticoagulant in the plugs. In certain embodiments, the exchange region is a gap between the delivery channel and the sampling or exit channel. In certain embodiments, the exchange region is the end of a set of concentric or side-by-side parallel channels.

The channels and/or exchange regions of a chemistrode can be a single monolithic part, or can be made of several parts reversibly joined together, such as by press-fit fittings, screw-fittings and the like. The exchange region may comprise a fitting for attachment to a container. In addition, portions of, or the entirety of the device may be disposable.

Preferably, the surfaces of delivery channels and sampling channels for transporting plugs are wetted preferentially by the carrier fluid over the plug fluid.

In certain embodiments, the portion of the channel for removing carrier fluid near the exchange region is wetted preferentially by the carrier fluid over the plug fluid. The exchange region can optionally have a membrane which allows selective mass transport between a plug and the environment. The surface properties of the exchange region can be engineered to control wetting and induce the breakup of plugs or the formation of plugs or to prevent the carrier fluid from escaping into the environment. For example, a portion of the inner surface of the exchange region can comprise a material that is preferentially wetted by the plug fluid to prevent the carrier fluid from escaping into the environment. In some embodiments, the inner surface of the exchange region can comprise a material that is hydrophilic. A portion of the inner surface of the exchange region can be made to be wetted preferentially by the carrier fluid to guide the flow of carrier fluid from a delivery channel to a sampling or exit channel. A portion of the inner surface of the exchange region can comprise a material that is wetted preferentially by the plug fluid to induce contact between the plug fluid and the environment.

For various embodiments, the delivery channel and the sampling or exit channel can be arranged at different angles to one another, or can be parallel to one another, or concentric with one other. A capillary divided in two half-moon formed channels by a separating wall, i.e., a so-called theta capillary, can be used. Multi-barreled capillaries can be used. If the channels are parallel to one another, they can be adjacent to one another, or separated by a distance. The delivery channel and sampling channel can be made of different materials.

As used herein, "mass transport" includes taking matter from the environment, leaving matter behind in the environment, or the exchange of matter between the environment and a plug. The mechanism for mass transport can vary, and includes but is not limited to diffusion, convection, diffusiophoresis, electrophoresis, and electroosmotic flow. Mass transport can also include, for example, self-propelled motion of microorganisms. In certain embodiments, mass transport can include the macroscopic movement of liquid, gas, or solid material, or mixtures thereof, into a sampling or exit channel. Preferably, when mass transport occurs, a detectable, and/or consequential, amount of matter is taken from, added to, or both taken from and added to, the environment.

"Matter" includes, but is not limited to, solutes, particles (both biological and non-biological, and nanoparticles), aerosols, gases, suspensions, slurries, molecules (including therapeutic drugs), a mixture of different molecules, polymers, ions, supramolecular assemblies, microemulsions, cells, microbial cells, organisms, stem cells, genetically engineered cells, clusters of cells and tissue fragments, and organelles.

"Plugs" in accordance with the present disclosure are formed in a channel on a substrate of a device when a stream of at least one plug fluid is introduced into the flow of a carrier-fluid in which the at least one plug fluid is substantially immiscible. The flow of the fluids in the device is induced by a driving force or stimulus that arises, directly or indirectly, from the presence or application of, for example, pressure, radiation, heat, vibration, sound waves, an electric field, or a magnetic field. Plugs in accordance with the present disclosure may vary in size. In certain embodiments, their cross-section is substantially similar to the cross-section of the channel. In other embodiments, their cross-section is smaller than the cross section of the channel. The cross-section of the plugs may vary. For example, when plugs merge or get trapped inside plug traps, the cross-section of the plugs may change. For another example, when a plug enters a wider channel, its cross-section may increase.

Further, plugs in accordance with the present disclosure may vary in shape, and for example may be spherical or non-spherical. The shape of the plug may be independent of the shape of the channel (e.g., a plug may be a deformed sphere traveling in a rectangular channel). The plugs may be in the form of plugs comprising an aqueous plug fluid containing one or more reagents and/or one or more products formed from a reaction of the reagents, wherein the aqueous plug fluid is surrounded by a non-polar or hydrophobic fluid such as an oil. The plugs may also be in the form of plugs comprising mainly a non-polar or hydrophobic fluid which is surrounded by an aqueous fluid. The plugs may be encased by one or more layers of molecules that comprise both hydrophobic and hydrophilic groups or moieties, such as surfactants. The term "plugs" also includes plugs comprising one or more smaller plugs, that is, plugs-within-plugs. The relative amounts of sample, reagents and reaction products contained in the plugs at any given time may depend on factors such as the extent of a reaction occurring within the plugs.

The term "plug fluid" refers to a fluid that is capable of dissolving or suspending matter to be delivered to or sampled from the environment, and which is substantially immiscible with the carrier fluid. Typically, the plug fluid comprises a solvent. The plug fluid may also comprise a reagent capable of reacting with matter sampled from the environment. The plug fluid may contain a surfactant.

Plug fluids can comprise essentially any fluid such as one or more gasses, aqueous solutions, one or more organic solutions, one or more inorganic solutions, or mixtures thereof, water, stock solutions, buffers, reagents, solvents, salt solutions, polymer solutions, precipitant solutions, metal suspensions, cell suspensions, or the like. Plugs can also comprise suspensions, emulsions, slurries, gels, dispersions, hydrogels, or fluid packets sampled from the environment.

The carrier fluid can be any liquid or gas that is substantially immiscible with the plug fluid. Preferably, when the plug is aqueous, the carrier is liquid. The surface tension of a plug fluid in a carrier is preferably between about 5-15 mN/m, preferably about 10 mN/m. Other non-zero values of the surface tension may be used. The carrier can be permeable to the plug fluid or reagents. In certain embodiments, the carrier fluid is fluorinated. Substances that can be used in the invention include but are not limited to fluorocarbons, perfluorocarbons, alkyl and aryl fluorocarbons, halofluorocarbons, fluorinated alcohols, fluorinated oils, liquid fluoropolymers including perfluoropolyethers, perfluorooctyl bromide, perfluorooctylethane, octadecafluorodecahydronaphthalene, 1-(1, 2, 2, 3, 3, 4, 4, 5, 5, 6, 6-undeca-fluorocyclohexyl)

ethanol, $C_6F_{11}C_2H_4OH$, Flourinert (3M), Krytox oils, Fomblin oils, Demnum oils, mineral oil and alkanes.

In some embodiments, it is desirable add a surfactant into the carrier fluid. Surfactant may be used to control the surface tension and the wetting properties of the carrier fluid. 1H,1H, 2H,2H-perfluorooctanol may be used as the surfactant when fluorinated fluids are used as carrier fluids. Surfactants may also be used to control non-specific adsorption of the contents of the plug to the interface between the plug and the carrier. For example, fluorous-soluble surfactants can be used to control non-specific protein adsorption at a fluorinated carrier-aqueous interface. An exemplary fluorous soluble surfactant is the oligoethylene glycol molecule triethyleneglycol mono [1H, 1H-perfluorooctyl]ether $CF_3(CF_2)_7CH_2O(CH_2CH_2O)_3H$). Other oil-soluble fluorosurfactants terminated with, or containing, oligoethylene groups may be used. Perfluorocarbons, perfluoropolyethers, and other fluorinated backbones may be used. Surfactants with well-defined composition can be used as well. Surfactants with the ability to resist non-specific adsorption can be extracted from commercially available Zonyl FSO-100 from DuPont via fluorous-aqueous extraction. Other oligoethylene glycol congeners with variable fluorinated alkane chain lengths, variable glycol lengths, and various spacer links can also be used to prevent protein adsorption at the aqueous-fluorous interface. Zwitterions, sugars, and other molecular components that confer to the surfactant ability to resist non-specific adsorption may be used. Conversely, surfactants capped with non-inert functional groups can attract and bind proteins to the liquid-liquid interface, including binding in a specific manner.

The terms "channel" or "microchannel" means a feature on or in an article (substrate) that at least partially directs the flow of a fluid. The channel can have any cross-sectional shape (circular, oval, triangular, irregular, square or rectangular, or the like). The channel may be open or closed. A channel may also have an aspect ratio (length to average cross sectional dimension) of at least 2:1, more typically at least 3:1, 5:1, or 10:1 or more. A channel may also include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. In one set of embodiments, the maximum cross-sectional dimension of the channel(s) containing embodiments of the invention are less than about 2 mm, less than about 1 mm, less than about 500 microns, less than about 200 microns, less than about 100 microns, less than about 50 microns, less than about 25 microns, less than about 10 microns, less than about 3 microns, less than about 1 micron, less than about 300 nm, less than about 100 nm, less than about 30 nm, or less than about 10 nm. The channel can be inside a capillary tube or other tubing, that is, a tube-shaped structure with a bore. The cross-sections of the tube and bore can be, for example, round, square or rectangular. The bore diameters can range in size from 1 micron to several millimeters; the outer diameters can be between about 60 microns or up to about several millimeters. The dimensions of the channel may also be chosen, for example, to allow a certain volumetric or linear flow rate of fluid in the channel. Of course, the number of channels and the shape of the channels can be varied by any method known to those of ordinary skill in the art. In some cases, more than one channel or capillary may be used.

Polymeric materials suitable for use with the invention are may be organic polymers. Such polymers may be homopolymers or copolymers, naturally occurring or synthetic, crosslinked or uncrosslinked. Specific polymers of interest include, but are not limited to, polyimides, polycarbonates, polyesters, polyamides, polyethers, polyurethanes, polyfluorocarbons, polystyrenes, poly(acrylonitrile-butadiene-styrene)(ABS), acrylate and acrylic acid polymers such as polymethyl methacrylate, and other substituted and unsubstituted polyolefins, and copolymers thereof.

Polyimide is of interest and has proven to be a highly desirable substrate material in a number of contexts. Polyimides are commercially available, e.g., under the tradename Kapton®, (DuPont, Wilmington, Del.) and Upilex® (Ube Industries, Ltd., Japan). Polyetheretherketones (PEEK) also exhibit desirable biofouling resistant properties. Polymeric materials suitable for use with the invention include silicone polymers, such as polydimethylsiloxane, and epoxy polymers.

The devices of the invention may also be fabricated from a "composite," i.e., a composition comprised of unlike materials. The composite may be a block composite, e.g., an A-B-A block composite, an A-B-C block composite, or the like. Alternatively, the composite may be a heterogeneous combination of materials, i.e., in which the materials are distinct from separate phases, or a homogeneous combination of unlike materials. As used herein, the term "composite" is used to include a "laminate" composite. A "laminate" refers to a composite material formed from several different bonded layers of identical or different materials. Other preferred composite substrates include polymer laminates, polymer-metal laminates, e.g., polymer coated with copper, a ceramic-in-metal or a polymer-in-metal composite. One preferred composite material is a polyimide laminate formed from a first layer of polyimide such as Kapton®, that has been co-extruded with a second, thin layer of a thermal adhesive form of polyimide known as KJ®, also available from DuPont (Wilmington, Del.).

The device can be fabricated using techniques such as compression molding, injection molding or vacuum molding, alone or in combination. Sufficiently hydrophobic material can be directly utilized after molding. Hydrophilic material can also be utilized, but may require additional surface modification. Further, the device can also be made from a variety of materials, including, but not limited to, plastics, metals, and glass. Microfabrication techniques can be employed to produce the device with sub-micrometer feature sizes. These include, but are not limited to, deep reactive ion etching of silicon, KOH etching of silicon, and HF etching of glass. Polydimethylsiloxane devices can also be fabricated using a machined, negative image stamp.

Environments with which the devices of the present disclosure can exchange matter can be, but are not limited to, solids, liquids, gasses, gels and/or surfaces, and combinations of any of these. The environment can be terrestrial or non-terrestrial. The environment may be an extreme environment such as deep-sea hydrothermal vents. Environment includes deep sea, marine sediments. Environments sensitive to contamination are also included. The environments can be living or non-living. The environments can be responsive or nonresponsive to stimuli. Living environments can be any organism, including, but are not limited to, humans, plants, fungi, tissue cultures, single cells, or communities of organisms, such as bacteria, including bacterial biofilms. The environment can be, for example, the skin or the intestine. The environment can be air. U.S. patent application Ser. No. 10/790, 936, hereby incorporated by reference herein in its entirety, describes typical airborne analytes.

U.S. Pat. No. 7,425,310, U.S. patent application Ser. Nos. 10/959,744, 11/952,943, and 11/056,247, and International Patent Application Publication No. WO03042699, hereby incorporated by reference herein in their entireties, describe examples of environments and analytes.

Certain embodiments of the invention may be used to stimulate all or part of an organism or to detect the presence of an organism. The term "organism" refers to any organisms or microorganism, including bacteria, yeast, fungi, viruses, protists (protozoan, micro-algae), archaebacteria, and eukaryotes. The term "organism" refers to living matter and viruses comprising nucleic acid that can be detected and identified, for example, by using PCR. Organisms include, but are not limited to, bacteria, archaea, prokaryotes, eukaryotes, viruses, protozoa, mycoplasma, fungi, and nematodes. Certain embodiments may be used to sample organisms from environmental sources including soil extracts, marine water, fresh water, marine sediments, freshwater sediments, hot springs, ice shelves, extraterrestrial samples, crevices of rocks, clouds, or particulates from aqueous environments.

Certain embodiments of the device may be used to obtain samples from a patient or person, including samples of blood, feces, urine, saliva or other bodily fluid. Food samples may also be analyzed. Environments for sampling include, but are not limited to geothermal and hydrothermal fields, acidic soils, sulfotara and boiling mud pots, pools, hot-springs and geysers where the enzymes are neutral to alkaline, tropical soil, temperate soil, arid soil, compost piles, manure piles, marine sediments, freshwater sediments, water concentrates, hypersaline and super-cooled sea ice, arctic tundra, the Sargasso sea, open ocean pelagic waters, marine snow, microbial mats (such as whale falls, springs and hydrothermal vents), insect and nematode gut microbial communities, plant endophytes, epiphytic water samples, industrial sites and ex situ enrichments. Additionally, a sample may be isolated from eukaryotes, prokaryotes, myxobacteria (epothilone), air, water, sediment, soil or rock, a plant sample, a food sample, a gut sample, a salivary sample, a blood sample, a sweat sample, a urine sample, a spinal fluid sample, a tissue sample, a vaginal swab, a stool sample, an amniotic fluid sample and/or a buccal mouthwash sample.

Certain embodiments of the invention can be used to deliver matter to or sample matter from aqueous or nonaqueous environments.

The devices of the present disclosure can be constructed in any form adapted for any intended use. In one embodiment, the device of the disclosure can be constructed as a disposable or reusable test stick to be contacted with a medium for which knowledge of the molecular environment is desired (e.g., an anatomical site, such as a wound site). In another embodiment, the device of the disclosure can be constructed using art recognized micro-scale manufacturing techniques to produce needle-like embodiments capable of being implanted or injected into an anatomical site for indwelling diagnostic applications. In other embodiments, devices intended for repeated laboratory use can be constructed in the form of an elongated probe.

The control and reproducibility provided by plug-based technology can be used to understand protein misfolding and aggregation structurally and functionally. Inert interfaces of plug-based systems eliminate non-specific nucleation of aggregation of Aβ peptides. See, for example, L. S. Roach, H. Song and R. F. Ismagilov, Anal. Chem., 2005, 77, 785-796; M. Meier, J. Kennedy-Darling, S. H. Choi, E. M. Norstrom, S. S. Sisodia and R. F. Ismagilov, Ismagilov, Angew. Chemie Int. Ed., 2009, 48, 1487-1489; J. E. Kreutz, L. Li, L. S. Roach, T. Hatakeyama and R. F. Ismagilov, J. Am. Chem. Soc., 2009, 131, 6042-6043; and C. Holtze, A. C. Rowat, J. J. Agresti, J. B. Hutchison, F. E. Angile, C. H. J. Schmitz, S. Koster, H. Duan, K. J. Humphry, R. A. Scanga, J. S. Johnson, D. Pisignano and D. A. Weitz, Lab Chip, 2008, 8, 1632-1639, all hereby incorporated by reference in their entireties.

The chemistrode can be used to sample aggregates from model organisms and deliver them to assays in plugs, and to inject back into the organism aggregates prepared in plugs.

The chemistrode provides a technology as general as the electrode to manipulate and observe biological systems, but at the chemical level. Also, the chemistrode provides a technology that provides high temporal and spatial resolution but can identify new molecules, monitor multiple molecular species simultaneously by independent techniques, and is not based exclusively on imaging.

For many biological systems it is preferred to use an array of local probes, and transmit minute volumes of solutions with no losses of sample or time resolution directly to analytical machines. The chemical version of the electrode, the chemistrode, provides a device for delivering pulses of chemical stimuli and collecting chemicals released in response thereto. The chemistrode is compatible with standard imaging techniques, and can be integrated with standard electrodes to simultaneously provide electrical and chemical stimulation and recording.

To overcome problems with single-phase fluid flow, the chemistrode can use microliter to femtoliter volume plugs to deliver stimuli and recover chemical responses, while controlling surface chemistry and eliminating dispersion, loss of sample and loss of time resolution. "Stimulus" and "collection" plugs can be delivered to the sample from a pre-formed array. An array of plugs comprises one or more plugs in a microchannel. The timing of delivery of each stimulus plug can be programmed by its position in the array. Arrays of thousands of plugs containing dozens of reagents at different concentrations can be generated by techniques known to those skilled in the art. The geometry, surface chemistry, and operating conditions at the exchange region of the chemistrode can be designed to promote break up of plugs into (a) an aqueous stream that can contact the sample, and in certain embodiments, deliver a stimuli to an environment and/or collect soluble species released from the environment in response, and (b) a carrier fluid stream that can remain in contact with an inner wall of a channel in the exchange region. Typically, in certain embodiments, in the exchange region the plugs are not completely surrounded by carrier fluid, but rather wet at least a portion of the environment, facilitating mass transport. Typically, in certain embodiments, when the second array of plugs enters the sampling or exit channel, the plugs are completely surrounded by carrier fluid.

Balancing pressure drops can also be important. Methods can be incorporated in the design of the device to overcome excessive pressure drop in the device due to high flow velocity or small cross-sectional dimensions of the flow path. To reduce the pressure drop in the delivery channel, multiple channels (each channel contains the fluid to be delivered) can be connected in parallel to the delivery channel. A switch device can be used to connect one of these channels to the delivery channel including but not limited to microfluidic valves (see, for example, U.S. patent application Ser. Nos. 09/894,857, 10/075,416, and 10/025,989, the entireties of all of which are hereby incorporated by reference) and oscillators (see for example, U.S. patent application Ser. No. 11/603, 030, the entirety of which is hereby incorporated by reference). When the fluid in the connected channels is flowed into the delivery channel, the switch device connects another channel to the delivery channel. This device reduces pressure drop by decreasing the length of the flow path. A similar design can be used to reduce the pressure drop in the sampling channel. Multiple channels can be connected to the sampling channel, and a switch device can be used to connect one of these channels to the sampling channel. When this channel is filled with the sampled fluid, the switch device connects another channel to the delivery channel. As the two fluids exit the exchange region of the chemistrode, the plugs can re-form to trap the released species. In certain embodiments, the timing of release of a substance from the environment can be determined by determining the position of the plug containing the substance in the array.

In certain embodiments, downstream of the exchange region, response plugs can then be split into a plurality of, for example, four or eight, parallel daughter arrays of smaller plugs, so each array can be analyzed by a different technique. Using techniques known in the art, plugs in each daughter array can be injected with a different set of reagents, as required for each analytical method. Results of all analyses can be combined and aligned to reconstruct the response of the system as a function of time. As long as the species released are sufficiently stable, subsequent analysis can be done off-line, at any speed, without substantial loss of time resolution. A number of analytical techniques are compatible with nanoliter or picoliter-sized plugs, including, for example, capillary electrophoresis, PCR, electrochemistry, mass-spectral methods, homogeneous and heterogeneous immunoassays, and fluorescence-based microscopies.

In one embodiment, a 200-µm scale chemistrode has been built and used to stimulate single murine islets with pulses of glucose and KCl, and to analyze the released insulin with time intervals of ~1.5 seconds. In addition to the applications of the chemistrode described in the respective sections above, the chemistrode can be used, for example, to understand paracrine signaling leading to secretion of glucagon from α-cells in islets of Langerhans. The chemistrode can be used to deliver stimuli believed to trigger glucagon release (switching from high to low glucose, and introducing gradients of $Zn^{2+}$ or insulin). For example, the sequences of species released at the surface (rich in α-cells) and ultimately in the interior of murine islets (rich in β-cells) can be recorded and analyzed to observe release of $Zn^{2+}$, GABA, insulin, somatostatin, and IAPP. The sequence of released species leading to glucagon release can be identified. This sequence can be recreated as an array of plugs, and re-applied to stimulate islets. Observing the absence of proper glucagon secretion would indicate that a component is missing (e.g., ATP) and would require further analysis. When proper glucagon response is observed, the missing components can be determined, and the sequence can be determined by eliminating components and switching the order in which they are delivered. Similar systems can be used to understand how dynamics of stimulation and release changes in the presence of other stimuli, such as circulating neurohormone epinephrine.

The chemistrode can achieve at least millisecond time resolution and at least sub-10-micrometer spatial resolution. 100 femtoliter plugs (approximately 5 µm in diameter) have been used in microfluidic devices, and sub-millisecond reactions have been used and mixing in plugs has been described. The chemistrode (optionally combined with an embedded electrode) can be used to understand the rich dynamics of neural and glial systems. The chemistrode can be used to stimulate and sample the extracellular chemical milieu of specific nuclear brain regions of organisms. For example, experiments can be conducted on a live zebra finch, a model organism in the study of learning and memory. Such experiments, optionally combined with stimulation and sampling of slices of living brain tissue, can provide insight into the modification of specific neuronal networks by neuromodulatory chemicals (cholinergic, adrenergic, dopaminergic) in response to auditory-feedback.

The chemistrode can decouple biological experiments from the "big machines" used for conventional analysis. In certain embodiments, neurobiologists can use the chemistrode to stimulate and sample their favorite region of the brain, and ship a frozen tube of response plugs for analysis, for example, receiving back overlaid graphs showing changes in concentrations of a plurality of classes of molecules with millisecond resolution. Beyond neuroscience, the chemistrode enables understanding dynamics in a wide range of other systems by sampling, identifying, and modulating intracellular and extracellular molecular signals in space and time.

In certain embodiments, the chemistrode allows delivery of a chemical stimulant to a substrate and subsequent sampling of the substrate with high temporal and spatial resolution. By using a prefabricated array of plugs containing stimulants in some of the plugs, time resolved chemical stimulation of the substrate can be achieved. The temporal resolution is determined by the time required for one plug to pass the substrate in the exchange region, and millisecond time resolution is possible. The spatial resolution of the device is determined by the diameter of the channels. In certain embodiments, a plurality of devices can be arranged in parallel. For example, two adjacent chemistrodes, comprising channels with an outer diameter of about 15 µm, can be used to stimulate and sample over a substrate region of about 30 µm in diameter.

The chemistrode is a chemical analogue of a microelectrode in some respects, but is capable of collecting numerous chemicals regardless of their electrical activity. The time-resolved sampling of live tissue and time-resolved delivery of chemicals to such a tissue can be used in diagnostics and treatments of diseases.

The chemistrode can locally apply sequences of chemical stimuli or drugs with millisecond temporal resolution, enabling studies of dosing dynamics to in vitro and in vivo biological samples. The chemistrode can be used in new drug therapies that require small dosages of drug delivered in specific temporal patterns. The flow in the chemistrode can be turned off and on, enabling irregular sampling patterns (for example, running every hour for 10 seconds and not running between the 10 second period).

Examples of biological experiments that can be conducted with various embodiments of the chemistrode include stimulating cells (e.g., cells of a frog Guinea pig ileum, leg, crayfish, Venus fly trap, *Pseudomonas* or muscle or a network of neurons) with a sequence of acetylcholine, curare, etc, and monitoring the action potential or physical movement. Certain embodiments can be used to stimulate at one place or cell, and watch the response at another place or cell. This experiment could be performed with a biofilm. The device can be used to sample over an ovule, and the plugs can be used to form a path guiding the growth of pollen tube. Certain embodiments can be used to control wing beat frequency on an insect. The chemistrode can be used to stimulate olfactory neurons in an organism, for example, *C. elegans*, while neurons are observed. Certain embodiments of the invention can be used to train organisms, e.g., *C. elegans*, by stimulating the organism with a certain sequence of stimuli encoded in an array of plugs, and punishing or reward the organism to determine if the organism can develop reactions to the chemical sequence. The device can be used for developmental experiments. For example the protein WINT can be delivered to a portion of a hydra to direct growth of a head.

The chemistrode can be used as a chemical defibrillator, for example by causing a heart attack or fibrillation in an organism by stimulating with plugs at two different places with different rhythms. One can defibrillate by stimulating the whole heart with one sequence of plugs. The device can be used to conduct analogous experiments with cultures of heart cells.

The chemistrode can be used to create chemical waves, for example by delivering alternating pulses of base and acid (in certain embodiments, the concentrations would increase) such that the diffusion of acid and base away from the exchange region forms oscillating waves of acid and base in the environment.

The chemistrode can be used to investigate catalytic surfaces, for example surfaces that change activity over time.

Multi-chemistrode arrays can be used to stimulate locally (one cell or a group of cells) and measure response in an adjacent cell or group of cells. This capability enables the study of communication between tissues on small time and length scales.

Samples collected in the plugs in the exchange region can be stored for off-line analysis without a loss of temporal information. Studies of protein crystallization show that plugs can be stored in glass capillaries for over half a year without a change of composition. The chemistrode can be placed on top of the substrate surface, or inserted into a live organ or tissue. For example, the chemistrode can be inserted into a certain part of the brain to deliver a plug of a drug solution, and to collect samples in plugs to monitor the response of the brain under the effect of the drug. Long-term (months or even years) of in vivo monitoring/studies can be performed using an implanted or an external sampler. This application is practically not possible with single-phase push-pull perfusion systems.

In certain embodiments, the collected response plugs can be reapplied as a sequence of stimulants to the same substrate at a different time point, or to a different location on the substrate (for example, one can stimulate the right side of a brain, then collect and reapply the response to the left side) and additional reagents can be added into the plugs before being reapplied to the substrate. The additional reagents may serve, for example, to extend the lifetime of response chemicals, or may react to remove a specific component of the chemical response. Such methods are useful in neurological studies.

The chemistrode can also be used to detect temporal biomarkers for disease in early stages. For example, some chemicals are always found in blood, but when their release profile changes, it can be an early sign of the development of certain diseases.

Certain embodiments of the device can be used for high throughput screening of drugs in vivo. Since the device can stimulate a small region on one or several cells using small volumes, it can be used to determine the effect of drugs on a particular type of cell without the threat of causing major harm to a system. This is especially useful for testing dangerous drugs, because it is better to apply them to one cell rather than to inject them into blood.

In certain embodiments of the device, samples collected in the plugs can be analyzed with conventional analytical tools, such as mass spectrometry, fluorescence microscopy, and capillary electrophoresis. Additional reagents such as fluorescent indicators can be introduced into the plugs by merging the plugs, using techniques known in the art, with a stream of the reagent to help analysis of the plugs. Trace amounts of chemicals, such as amyloid-β-derived diffusible ligand (ADDL), can be detected by an autocatalytic amplification method. The array of plugs collected from the device can also be split into two or more identical smaller arrays, allowing multiple analytical techniques to be applied on a single time point.

In certain embodiments, a thin membrane can be incorporated in the exchange region of the device to reduce the shear stress applied to the environment. This can be useful for experiments in live tissue. Excessive shear stress may be harmful to the environment to be sampled. In certain embodiments, the membrane can be used to remove unwanted solid material that could clog the exchange region and or sampling or exit channel. A thin membrane between the exchange region and the environment can protect the environment to be sampled from being damaged by shear stress and can prevent solid materials with dimensions above the membrane pore size from entering the sampling channel. The membrane should allow efficient mass transport between the exchange region and the environment. Mass transfer could be improved by using very thin membranes and membranes with high porosity. The surface chemistry of the membrane could be used to control selective passage of one-phase of fluid through the membrane while preventing the other phase from crossing the membrane.

For example, a hydrophilic membrane may allow selective passage of aqueous solutions. Examples of using surface chemistry to separate gasses and liquids are described in Gunther A., Jhunjhunwala M., Thalmann M., Schmidt, M. A. Jensen, K. F., "Micromixing of miscible liquids in segmented gas-liquid flow", Langmuir, 21(4), 1547-1555, 2005, the entirety of which is hereby incorporated by reference. Examples of liquid-liquid separations are described in "Phase separation of gas-liquid and liquid-liquid microflows in microchips," Microchimica Acta, 164(3-4), 249-255, 2009, the entirety of which is hereby incorporated by reference. The membrane could be manufactured from materials including, but not limited to, thin films, silicon nitride, silicone, Teflon AF, porous oxides, porous metals, PDMS, Nafion, ceramics, cellulose acetates, polyether sulfones, polyacrilonitriles, polyamide, polyimide, polyethylene, polypropylene, polytetrafluoroethylene (PTFE, Teflon), polyvinylidinefluoride, and polyvinylchloride. The gradient of pressure in the device may also drive convective flow that improves mass transfer through the membrane.

In certain embodiments, the chemistrode can switch between a channel which is used for delivery and a channel which is used for sampling. It can also "record" and "replay" on the same device. The device may use a specific microchannel channel first for delivery, then for sampling. This approach requires only one channel but still requires an exchange region. Spatially-dependent operation of the chemistrode is also possible. For example, the chemistrode may be used in conjunction with an array or as a scanning device. This approach would involve moving the device relative to the environment.

Referring to FIG. 1, a device for delivering plugs to the exchange region is shown. Plugs come in via the delivery channel, and the sampling or exit channel removes the carrier fluid and is substantially free of plugs. There may be occasional plugs removed via the sampling channel.

In certain embodiments, the delivery channel is a piece of tubing, for example made from PTFE, or Teflon, for delivering plugs in a carrier fluid. The PTFE tubing may be placed in a fused silica capillary; and the space between the Teflon tubing and the fused silica capillary form the sampling channel for removing the carrier fluid. The inner surface of the delivery channel may be hydrophobic to facilitate the transport of plugs. To facilitate selective removal of the carrier fluid, the surfaces of the sampling channel (which include the outer surface of PTFE tubing and the inner surface of fused silica capillary) may be made hydrophobic. The hydrophobic surface attracts the carrier fluid into the sampling channel while at the same time repels the plug fluid from entering the sampling channel. The fused silica capillary may be made hydrophobic by functionalization using a perfluorinated silane. Optionally there is an off-set between the fused silica capillary and the Teflon tubing, in which the Teflon tubing may have a section sticking out of the fused silica capillary which helps coalescence of the plugs with the bulk of environmental solution.

Optionally the flow rate in the delivery channel and the sampling channel can be balanced to help allow most of the carrier fluid to be removed via the sampling channel while the plug fluid is delivered into the environment. For example, in a particular experiment, the total flow rate in the delivery channel was about 1 µL/min and the carrier fluid took up about half of the volume in the plug-flow, so a flow rate of about 0.5 µL/min was used for the sampling channel.

Figure 2:
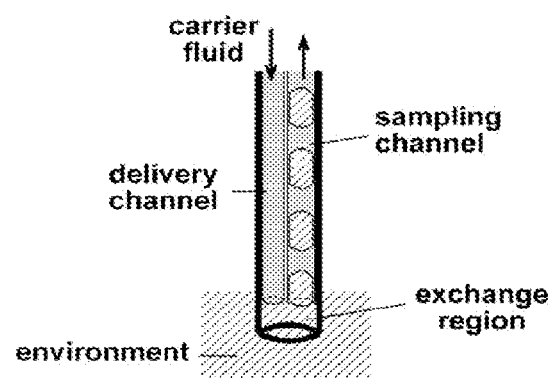
FIG. 2 is an illustrative view of a device for forming plugs using plug fluid provided from the environment.

Referring to FIG. 2, a device for forming plugs using plug fluid provided from the environment is shown. In this device, the inner surface of the sampling channel is preferentially wetted by the carrier fluid to facilitate formation and transport of plugs. Optionally, the inner surface of the exchange region is preferentially wetted by the plug fluid, in order to promote sufficient contact between the plug and the environment as well as to prevent the carrier fluid from escaping from the device. The volumetric flow rate in the sampling or exit channel may be made higher than the flow rate in the delivery channel. Optionally, the volumetric flow rates may be substantially identical, and carrier fluid may be lost to the environment, for example, by evaporation.

Figure 3:
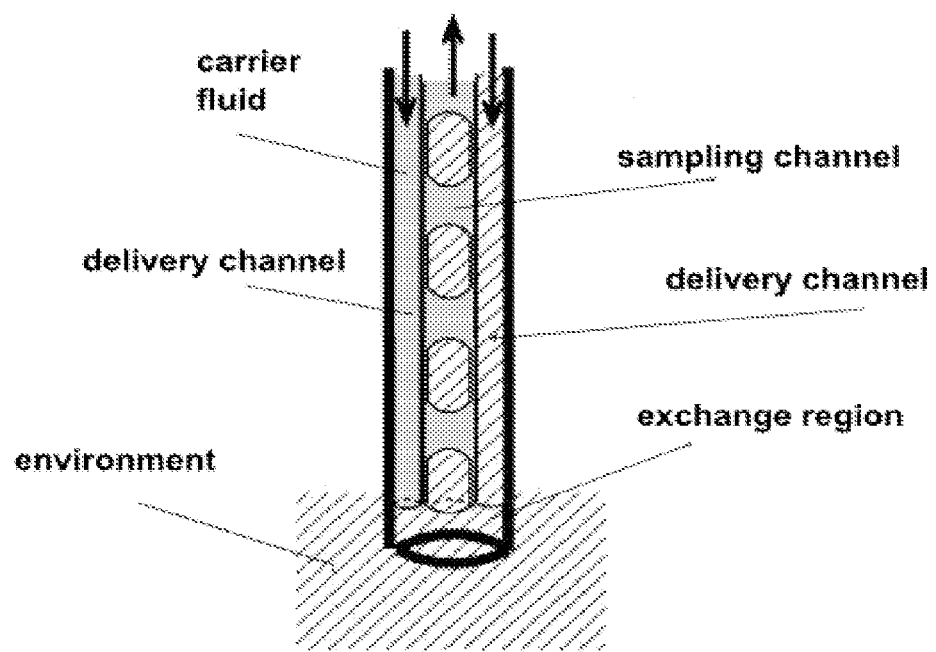
FIG. 3 is an illustrative view of a device in which a carrier fluid and a plug fluid are introduced to the exchange region of the device via separate delivery channels and plugs are produced at the exchange region.

Referring to FIG. 3, a carrier fluid and a plug fluid are introduced to the exchange region of a device via separate delivery channels and plugs are produced at the exchange region.

Figure 4:
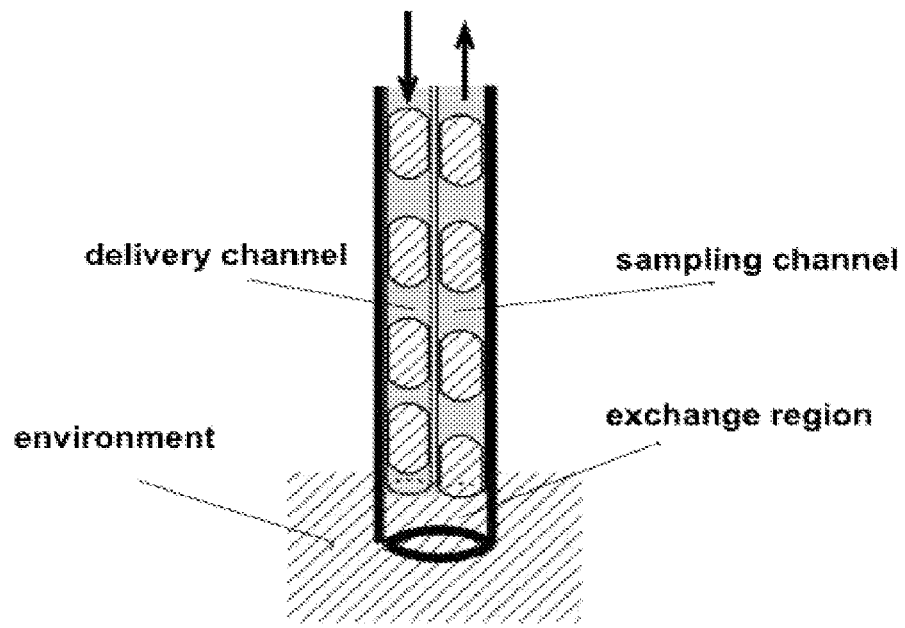
FIG. 4 is an illustrative view of a device in which a plurality of first plugs is introduced to the exchange region of the device and a plurality of second plugs is produced at the exchange region.

Referring to FIG. 4, a plurality of first plugs is introduced to the exchange region of a device and a plurality of second plugs is produced at the exchange region. The inner surfaces of both the delivery and sampling or exit channels are preferentially wetted by the carrier fluid. In this device, a majority of the carrier fluid entering the delivery channel also enters the sampling or exit channel. To prevent the carrier fluid from leaking into the environment, several methods can be used. For example, if the "environment" is a solid or gel, the exchange region can comprise a seal capable of sealing off a portion of the environment from the remainder of the environment, preventing the carrier fluid from leaking. This seal can be formed, for example, by applying pressure on the device against the environment, or applying adhesive at the bottom of the exchange region, or applying a thin membrane that selectively allows only aqueous materials to cross the membrane while prevents carrier fluid from escaping.

Figure 5:
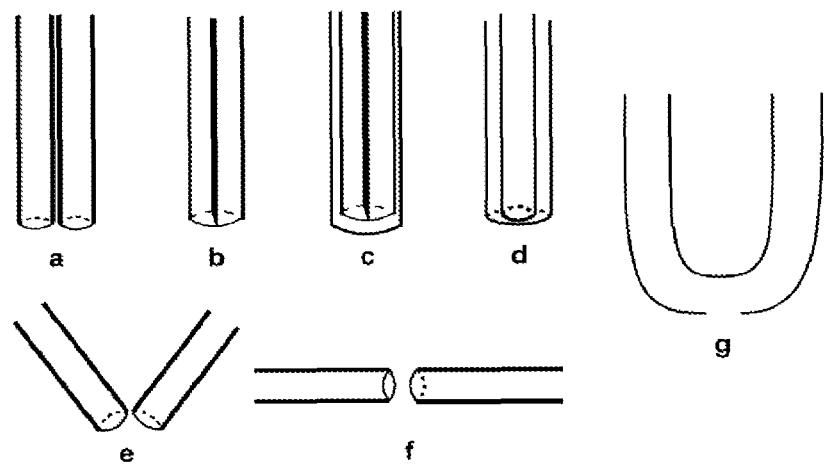
FIG. 5 is an illustrative view of exemplary arrangements of microchannels.

Referring to FIG. 5, exemplary arrangements of microfluidic channels are shown.

Figure 6:
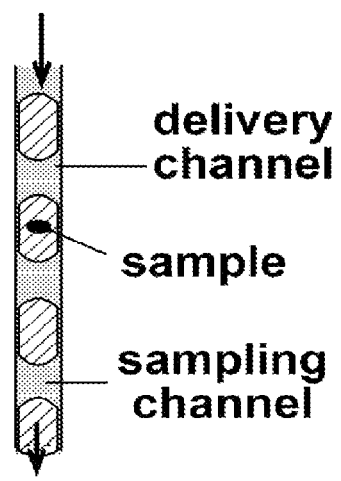
FIG. 6 is an illustrative view of another chemistrode.

Referring to FIG. 6, in certain embodiments, the sample to be analyzed is held inside a closed channel. The delivery channel is the section of channel upstream of the sample; the sampling, or exit channel is the section of channel downstream of the sample. The exchange region is the location of the sample. The sample may be, for example, held suspended in the channel using electrophoretic forces, it may be attached to the walls of the channel, or it may sit on a membrane inside the channel. Other means may be used to maintain the sample in the channel. Plugs come in from the delivery channel, and mass transfer takes place between the sample and the plug, and the sampling or exit channel removes the plugs.

Figure 7:
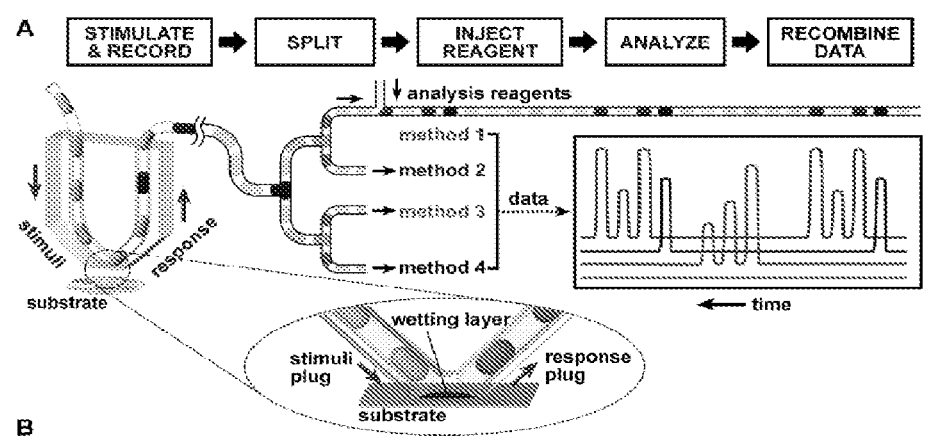
FIG. 7 is an illustrative view of a chemistrode that delivers and records multiple chemical signals with high temporal and spatial resolution for off-line analysis by multiple analytical methods in parallel and a conceptual schematic drawing of stimulation, recording, and analysis.

Referring to FIG. 7, in certain embodiments, the chemistrode enables local delivery of pulses of chemical stimuli, local collection of molecules released in response, and transport of these molecules for analysis by multiple methods in parallel, all with high chemical, spatial, and temporal resolution.

In certain embodiments, the chemistrode uses multiphase microfluidics to compartmentalize chemical signals in plugs. In certain embodiments, aqueous plugs nanoliters in volume surrounded by a fluorocarbon carrier fluid, to reduce dispersion and loss of sample due to surface adsorption, are used. In certain embodiments, the chemistrode is designed to contact and exchange signals between the device and a thin aqueous wetting layer above the substrate. In certain embodiments, operation of the chemistrode is similar to that of an electrode; it is simply brought into contact with the surface under investigation. Using the chemistrode in certain embodiments, instead of exchanging electrical signals as does an electrode, the molecules contained in "stimulus plugs" are exchanged and molecules released into the wetting layer are captured by "response plugs".

Still referring to FIG. 7, in some embodiments, typical operation of the chemistrode can comprise nine general steps: (i) preparation of an array of aqueous plugs containing an arbitrary sequence of stimuli, (ii) delivery of the array of stimulus plugs through a delivery channel to a hydrophilic substrate, (iii) coalescence of stimulus plugs with the wetting layer above the hydrophilic substrate, while the fluorocarbon carrier fluid remains in contact with the wall of the chemistrode in the exchange region; (iv) rapid exchange in the exchange region of diffusible signals between the plug and the thin layer of wetting fluid on the substrate, (v) re-formation of plugs containing response molecules released by the substrate, (vi) delivery of response plugs, via a sampling or exit channel, to a splitting junction to form identical daughter arrays, (vii) injection of each daughter array with reagents required for further analysis, (viii) analysis of each daughter array by a different technique, and (ix) final recombination of data from the analysis of daughter arrays to provide a time-resolved analysis of chemical stimulation and response dynamics. In certain embodiments, some of these steps are omitted. For example, in certain embodiments, no stimulus plugs are used. For certain experiments, alternative stimuli, for example, exposure to light, could be used, or no stimuli could be used.

Optionally, the plugs can be sorted before or after splitting downstream of the exchange region, for example in order to analyze only those plugs displaying a certain characteristic (for example, a fluorescence assay could be performed, and then only those cells that are positive for the analyte could be further analyzed). Techniques for sorting plugs are known in the art. For example, every x-th plug could be analyzed by each method, such as by redirecting plugs into x channels (e.g., the 1st, 5th, 9th plugs go into a first channel, the 2nd, 6th, 10th into a second, etc.).

Still referring to FIG. 7, a chemistrode delivers and records multiple chemical signals with high temporal and spatial resolution for off-line analysis by multiple analytical methods in parallel. A conceptual schematic drawing of stimulation, recording, and analysis is shown as well.

The concept as outlined in FIG. 7 was demonstrated by fabricating a chemistrode with about 200×200 µm channels (cross sectional dimensions) by using rapid prototyping in poly(dimethylsiloxane) (PDMS). Microchannels were rendered hydrophobic and fluorophilic using silanization. In one embodiment, Teflon tubing was inserted into the channels as shown in FIG. 7B. The gap between the Teflon tubing and surrounding PDMS was filled with half-cured PDMS glue (Dow-Corning Sylgard 184 A and B at a ratio of about 10:1, cured at about 110° C. for about 110 s), and then the device was baked at about 65° C. for the PDMS glue to fully cure. The tip of the chemistrode can be cut smaller, typically with a bottom area of ~1×0.6 mm, to reduce the outer dimension. The preparation of arrays of plugs containing arbitrary reagents and concentrations for delivery to the substrate and their transport through fluorophilic channels to the exchange region was carried out by techniques known in the art.

To enhance coalescence, flow can be confined within a V-shaped geometry of the chemistrode. Coalescence can be accelerated by using carrier fluids with low viscosity that can drain on the sub-millisecond time scale and do not limit the temporal resolution. Also, a small-molecule surfactant, for example, triethyleneglycol mono[1H,1H-perfluorooctyl] ether, can be used to provide desirable surface tension and sufficiently rapid dynamics to provide reliable frequencies of coalescence, for example, $f_{coal} > \sim 50$ $s^{-1}$, while preventing non-specific protein adsorption to the aqueous-fluorous interface.

The chemistrode enables delivery of arbitrary sequences of multiple chemical reagents as pulses of controlled intensity and duration at high temporal resolution. To quantify the efficiency of delivery of a stimulus, plugs of only two fluorescent dyes were delivered. High-speed confocal microscopy enabled imaging of the wetting layer on the surface with two wavelengths simultaneously. In normal operation of certain embodiments, arrays of dozens of reagents could be delivered to the substrate. This experiment confirmed efficient delivery of the reagents into the wetting layer. Short pulses with a duration of ~50 ms were encoded in individual plugs. Higher intensity pulses were encoded with plugs containing the reagent at higher concentration. Longer pulses could be encoded with longer plugs, but since long plugs may break up spontaneously, encoding with sequences of short plugs is preferred. The pre-determined sequence of plugs was delivered three times with high reproducibility. These results also demonstrated that the chemistrode is compatible with standard optical imaging techniques.

The chemistrode can provide efficient recording of released signals, superior to single-phase laminar flow. Pulses of fluorescein were generated by using a microinjector to pulse the solution out of the tip of a glass capillary that ended flush with a PDMS surface. The chemistrode was placed over the tip of the capillary. The shortest pulse was ~40 ms with a volume of ~0.2 nL. These pulses were repeated every ~1 second. Pulses were collected by using either the plug-based flow of the chemistrode or single-phase laminar flow in the same geometry. In both cases, the fluorescence intensity was detected at a second point close to and downstream of the tip (the exchange region) of the chemistrode and at a second point ~10 cm downstream of the tip by using high-speed fluorescent video microscopy. In these experiments, fluorescence was not measured simultaneously at both sites. Recording with single-phase laminar flow resulted in poor temporal resolution and poor efficiency of collection. Broadening of the fluorescent peaks was already visible at the point near the tip of the device, and the intensity of the signal decreased more than ~100-fold after traveling ~10 cm downstream (to the second point) due to dispersion. On the other hand, the chemistrode demonstrated high efficiency of recording. Plugs re-formed reliably in the exchange region and captured the pulse. At the first point, fluorescent signal was distributed over no more than two plugs, while recirculation within plugs redistributed the contents of the pulse, causing the measured signal to fluctuate in some of the plugs. The recorded signal was transported ~10 cm with no losses of temporal resolution, and appeared as a smooth peak, because fluorescein was mixed by the recirculation within the plug.

To test whether a chemistrode provides chemical stimulation and recording with high spatial resolution, multilayer soft lithography was used to fabricate two chemistrodes with ~25 μm channels separated by a thin, ~20 μm layer of PDMS. To generate pulses of different chemical composition in close proximity on a hydrophilic, PDMS surface, a microfluidic device was used to eject any of three solutions to the surface through two ~25×15-μm orifices spaced ~20 μm apart. These solutions were buffer (colorless), fluorescein (green), and 8-methoxypyrene-1,3,6-trisulfonic acid (MPTS, blue). The recorded signal was monitored at two sites: near the tip of the chemistrode and ~7 cm downstream. The two-layer chemistrode reliably recorded the sequences of pulses at both locations with no cross-contamination and no loss of intensity during transport. The use of plugs was essential—when single-phase flow was used instead, pulses rapidly broadened, overlapped and decayed. In these small channels, Taylor dispersion was less severe, but losses to the walls of channels became pronounced, especially when testing solutions of proteins. Here, to separate the effect of transport and dispersion from the effect of adsorption, two fluorescent dyes were selected that did not undergo severe adsorption. The chemistrode transported substantially even molecules that tended to adsorb to PDMS and Teflon.

To test the compatibility of a chemistrode with off-line multi-analyte measurements by independent methods, a chemistrode was used to record pulses of a mixture of four compounds—$CaCl_2$, insulin, glucose, and MPTS as a positive control—each representing a different class of molecules and detectable by a different technique. The array of recorded response plugs was split into four identical daughter arrays. Each plug in the first daughter array was injected with a fluorescent indicator, fluo-4. Measuring fluorescence of the fluo-4-$Ca^{2+}$ complex of each plug in this array detected the presence of $Ca^{2+}$ ions and provided a profile of $Ca^{2+}$ release as a function of time. In parallel, plugs in the second array were injected with the mixture of an anti-insulin antibody and labeled insulin for a competitive immunoassay. Control experiments indicated that plugs provide an excellent transport and storage medium for insulin for off-line analysis, with no losses of insulin due to degradation or adsorption to surfaces, in contrast to almost complete loss of insulin from laminar flow in the same Teflon tube. To determine the concentration of insulin, the fraction of labeled insulin that was free or bound to the antibody was detected by using Fluorescence Correlation Spectroscopy (FCS). Plugs in the third array were injected with Girard's T reagent ((Carboxymethyl)trimethylammonium chloride hydrazide) and incubated overnight to give a hydrazone derivative of glucose, and the presence of the hydrazone was then detected by MALDI MS. MALDI MS is an example of a method that can detect unknown molecules. As a control, fluorescence of MPTS was measured in the fourth array. Final recombination of data from all four analyses showed good alignment among different techniques and with the positive control trace of MPTS.

In certain embodiments, splitting followed by off-line analysis is an attractive feature of the chemistrode that decouples the stimulating and recording experiment from the equipment and expertise that may be required for analysis of nanoliter volumes. Decoupling in time was demonstrated; while the chemical signals were recorded on the time scale of seconds, incubation and measurement steps during analysis took over 24 hours but did not lead to loss of signal or time resolution. Decoupling in location was also demonstrated;

recording with a chemistrode was demonstrated in a first lab, and plugs were then analyzed for insulin one day later using an FCS instrument located in a second lab 20 miles away. Control experiments indicated that storage and transportation of tubing containing response plugs did not affect the time resolution or quality of analysis by FCS. Arrays of plugs have been successfully shipped cross-country, or frozen and thawed without disruption.

In addition, the compatibility of a chemistrode with live-cell experiments was tested. Fluorocarbons are compatible with live cells and tissues. In addition, the carrier fluid does not contact the cells and wets the walls of the chemistrode instead. For the test, mouse islet of Langerhans, a model system widely studied in the context of diabetes, was used. A chemistrode was used to stimulate single islets by a transition from a low-glucose buffer (~2 mM glucose) to a high-glucose buffer (~14 mM glucose). The increase of intracellular $[Ca^{2+}]_i$ by islets in response to glucose stimulation was optically monitored by measuring the fluorescence intensity of a fluorescent calcium indicator, fluo-4. During stimulation, islets displayed the expected $[Ca^{2+}]_i$ response: a slight decrease followed by a sharp increase of $[Ca^{2+}]_i$, which gradually decreased and started regular oscillations. This response was reproduced for different batches of healthy islets and agreed with the response observed in control experiments, confirming that the chemistrode did not introduce artifacts.

In certain embodiments, the chemistrode provides an opportunity to understand local chemical dynamics of stimulus-responsive matter. In chemistry and material science, this matter ranges from catalytic surfaces, smart materials, and materials for active release. Biological systems are intrinsically responsive to stimuli and display non-trivial spatial dynamics on levels ranging from networks, to cells to tissues. Using microelectrodes, electrical pulses from a person's neuron system have been recorded and replayed on another individual for interfacing neural systems of two humans, or used to control robotics for interfacing human thought and machine. The chemistrode is a chemical counterpart of these microelectrodes. Nanoporous membranes can be integrated to reduce the shear experienced by the substrate, while providing rapid mass transfer between the substrate and the plugs. Pressure-sensitive valves can be incorporated to balance pressure at the substrate. Mechanically stable microprobes can be fabricated for insertion into tissues.

Prefabricated holders (e.g., cartridges or capillaries) of plugs ("holding components") can be manufactured with arrays of plugs containing reagents for adding to a sample (e.g., a range of concentration of materials for stimulating various cell types, or various compounds). More is described in U.S. patent application Ser. No. 11/174,298, incorporated by reference herein in its entirety. Kits of such holding components can be manufactured. Similarly, plugs can be stored for later sampling in a "loading component".

EXAMPLE 1

Unless otherwise stated, all chemicals were purchased from Sigma-Aldrich at standard grades. $R_fOEG$ (triethyleneglycol mono[1H,1H-perfluorooctyl]ether) was prepared according to published procedures. Human insulin (product number I2643) and BSA (product number A3059) were purchased from Sigma-Aldrich. Monoclonal antibody to human insulin (catalogue number E86307M) was purchased from Meridian Life Science. Tween® 20 (product number BP337-100) and 2,5-dihydroxybenzoic acid were purchased from Acros Organics. Alexa Fluor® 488 5-TFP (catalogue number A-30005), cell-impermeant fluo-4 pentapotassium salt (catalogue number F-14200), cell-permeant fluo-4 AM ester (catalogue number F-14217), and dextran Alexa Fluor® 594 (catalogue number D-22913) were purchased from Invitrogen. Chelex® 100 Resin was purchased from Bio-Rad Laboratories. 8-methoxypyrene-1,3,6-trisulfonic acid (MPTS) was purchased from Invitrogen. PTFE tubing was purchased from Zeus Industrial Products.

Properties of all the aqueous solutions, including PBS (1x, pH ~7.4) buffer and potassium phosphate buffer (~0.032 M, pH=~8.2), were estimated as the values of water at room temperature. Viscosity and density of all the aqueous solutions are estimated as $~10^{-3}$ kg/(m·s) and $10^3$ kg/m$^3$, respectively.

Viscosity and density of FC3283 at room temperature are $~1.4\times10^{-3}$ kg/(m·s) and $~1.834\times10^3$ kg/m$^3$.

All the PDMS microfluidic devices with rectangular cross sections were fabricated by rapid prototyping soft lithography. The surfaces of the PDMS microchannels were made hydrophobic and fluorophilic by functionalization with (tridecafluoro-1,1,2,2-tetrahydrooctyl)-1-trichlorosilane.

Plugs were generated in PDMS microchannels with a cross geometry and rectangular cross sections of ~100 µm×100 µm. The carrier fluid was ~0.5 mg/mL $R_fOEG$ dissolved in FC3283. Two aqueous streams were used: one stream contained only the buffer (~0.032 M potassium phosphate, pH=8.2) and the other contained ~140 µM fluorescein dissolved in the same buffer. To generate repeated arrays of a single fluorescent plug followed by ~20 non-fluorescent plugs, the carrier fluid stream was kept running continuously while a Labview program was used to rapidly switch on/off the two aqueous streams. At any time, only one aqueous stream was running. The flow rate was ~4 µl/min for both carrier fluid and aqueous stream, and the total flow rate was ~8 µl/min. The resulting plugs were delivered to the chemistrode through PTFE tubing with i.d./o.d. ~200 µm/250 µm. Images were taken using a high speed camera (Phantom, Vision Research, Stuart, Fla.) at ~1000 fps.

EXAMPLE 2

A sequence of plugs was generated in a piece of PTFE (I.D. ~237.5 µm). Light green, dark green, light red, and dark red plugs contained ~10 µM fluorescein, ~20 µM fluorescein, ~10 µM sulforhodamine 101, and ~20 µM sulforhodamine 101, respectively. Gray plugs contained only the buffer. The volume of each aqueous plug and each carrier fluidic spacing between two plugs was ~30 nL. The carrier fluid was FC3283 with ~0.5 mg/mL $R_fOEG$. Buffer for all aqueous solutions was ~0.032 M potassium phosphate buffer, pH ~8.2. One cartridge of plugs could contain multiple periods of the sequence. The chemistrode was pressed to a glass slide (Fisherbrand, ~75×50×1 mm). This slide was plasma oxidized prior to the experiment, making its surface hydrophilic. Plugs in the preformed cartridge were flowed into the chemistrode at a flow rate of ~80 µl/min (flow velocity=~0.03 m/s).

A Leica SP5 tandem scanner spectral 2-photon confocal microscope was used to obtain fluorescence data with the following settings:
ScanMode: xt
Pinhole (Airy): 1.3
Zoom: 4.9
Objective: HCX PL APO CS10.0×0.40 DRY UV
Laser Lines: 488 nm Ar, 561 nm diode
Emission bandwidths: 500.0 nm-545.0 nm, 600.2 nm-720.1 nm
PMT output: 8-bit A Leica LAS AF Lite (1.7.0 biult 1240) was used to control the microscope and analyze the data. The focus was adjusted on the surface of the glass slide, as determined by reflected light. The scan rate was ~8000 lines per second. Every eight lines were averaged for one recording time point. Two beams of laser (~488 nm, ~561 nm) were switched by an acoustic optical tunable filter (AOTF). Emission light of ~500.0 nm-545.0 nm and ~600.2 nm-720.1 nm was detected by two photomultiplier tube (PMT) fluorescence detectors. Fluorescence intensities of both fluorescein and sulforhodamine 101 were averaged on the center 50% (corresponding to a physical length of about 150 μm) along the lengths of line scans, assuming that region of interest responding to the stimuli is located in the centre of the area under the tip of the chemistrode.

EXAMPLE 3

A 5 cm long fused silica capillary tubing with a square cross-section (~50 μm inner edge length., ~363 μm outer edge length, Polymicro Technologies, Phoenix, Ariz.) was placed in a PDMS channel. The hydrophilic cross section (~300×300 μm square glass surface with ~50 I.D. puffing orifices) of one end of this capillary was aligned to the tip of the chemistrode to serve as the substrate. The gap between the capillary and surrounding PDMS was filled with half-cured PDMS (Dow Corning Sylgard 184 A and B at a ratio of ~10:1, cured at ~110° C. for ~110 s) followed by baking at ~65° C. to prevent fluid leakage. The other end of the silica capillary was connected to a ~20 cm long ~300 μm I.D. Teflon tubing filled with fluorescein ~500 μM, and connected to a microinjector (IM300, Narishige, Japan). The microinjector injected multiple pulses of fluorescein solution into the chemistrode with well defined injection time and intervals. A LabVIEW program was used to control the microinjector for automatic operation. The duration for each injection was ~40±2 ms as measured according to a recorded movie. The time interval between consecutive pulses was set to ~1 s.

The stimulus plugs were formed by flowing a carrier fluid stream (~0.5 mg/mL $R_fOEG$ in FC3283) and an aqueous stream (1×PBS buffer at pH ~7.4) into a T-junction device at the equal volumetric flow rate of ~16 μL/min. The total flow rate was ~32 μL/min. Pulses of fluorescein collected by plugs in the chemistrode were detected at two positions: the tip of the chemistrode and ~10 cm downstream. The detection results from the chemistrode were compared to that from the single phase laminar flow at the same sites and with the same flow rate, ~32 μL/min. The fluorescence microscopic images and movie were taken by using a high speed camera (Phantom, Vision Research, Stuart, Fla.).

The device for the high spatial resolution experiment was fabricated using multi-layer soft lithography. Two molds with mirrored channel designs were made. The channels had uniform thicknesses of ~25 μm and widths of ~15-25 μm. Dow Corning Sylgard 184 A and B components were mixed at a mass ratio of ~5:1 and poured onto the mold for the top layer to a thickness of ~5 mm, and was incubated in the oven at ~65° C. for ~30 min. A ~20:1 mixture of A and B was spin-coated onto the mold for the second layer pattern at ~3600 rpm for ~30 s, which resulted in a membrane with a thickness of ~40 μm comprising a ~15 μm thick PDMS layer over the ~25 μm channel patterns. After curing at ~65° C. for ~25 min, the membrane layer was aligned to the top layer with MJB3 contact Mask Aligner (Karl Suss), and cured at ~65° C. for another ~15 min. The bonded layers were pealed off from the mold, punched with access holes, sealed to a ~1 mm thick ~5:1 (A:B) flat layer (pre-incubated the same as top layer), and baked in a ~65° C. oven overnight. The sealed device was cut with a sharp blade under a microscope.

The following steps described the process to make the puffing channels hydrophilic but keep the chemistrode fluorophilic. A piece of adhesive tape was inserted into the slot between the upper chemistrode part and the lower puffing part to isolate them before the treatment. FC3283/PFO (~5:1 v/v) was infused into the chemistrode channels at ~0.10 μL/min for ~20 minutes to saturate the PDMS surface with oil-phase surfactant before flowing aqueous solution. ~5 mg/mL BSA solution in 1×PBS buffer (pH ~7.4) was infused into the puffing channels with a flow rate of ~0.1 μL/min for ~30 minutes to make puffing channels hydrophilic, and the puffing channels were rinsed with PBS buffer to flush away residual BSA. Then, the adhesive tape insert was removed and the device was ready for use.

For spatial resolution experiments, a clamp was used to hold the chemistrode and the puffing part together to avoid leakage at the interface between the two parts. Syringes filled with solution and carrier fluid were connected to the device via Teflon tubing and driven by four syringe pumps (PHD2000, Harvard Apparatus) controlled by a LabVIEW program. An adjustable vacuum (~0 to ~750 mmHg) was connected to the channel outlet to reduce the pressure drop at the tip of the chemistrode. The stimulus plugs were formed by flowing a carrier fluid stream (~20% v/v PFO in FC3283) and an aqueous stream (1×PBS buffer pH ~7.4) into the T-junction at flow rates of ~0.75 μL/min and ~0.75 μL/min, respectively. For fluorescence measurements, a Leica DMIRE2 microscope with a digital camera (ORCA-ER, Hamamatsu) was employed. GFP and DAPI filter cubes were used to observe the fluorescence of fluorescein and MPTS, respectively. Flow rates and puffing procedures were controlled with a LabVIEW program.

EXAMPLE 4

Preparation of Solutions

~25 mM HEPES buffer was made by diluting ~0.1 M HEPES buffer (pH=~7.35) with Millipore filtered water. This HEPES buffer was stirred with Chelex® 100 Resin for one hour to remove the background $Ca^{2+}$ ions. A solution of ~0.1% Tween 20 in ~25 mM HEPES buffer was treated by Chelex® 100 Resin with the same protocol. Sample solution contained ~250 μM $CaCl_2$, ~500 nM insulin, ~20 MPTS, ~50 mM Glucose, and ~0.1% Tween® 20 in ~25 mM HEPES buffer. All solutions were filtered with ~0.45 μm medium PTFE syringe filters (Fisher Scientific) before being used.

Injecting Pulses of Chemicals into the Chemistrode

The stimulus plugs were formed by flowing a carrier fluid stream (~0.5 mg/mL $R_fOEG$ in FC3283) and an aqueous stream (~25 mM HEPES buffer, pH ~7.35) into a T-junction device at flow rates of ~2.0 μL/min and ~2.5 μL/min, respectively. The resulting plugs were transported to the chemistrode device at a total flow rate of ~4.5 μL/min. Pulses of chemicals were injected into the chemistrode through a Y-shaped device whose hydrophilic surface with an outlet channel was aligned against the bottom of the chemistrode. Alternating pulses of buffer (~0.1% Tween 20 in ~25 mM HEPES buffer, pH v7.35) or sample solution (=250 μM $CaCl_2$, ~500 nM human insulin, ~20 μM MPTS, ~50 mM glucose and ~0.1% Tween 20 in ~25 mM HEPES, pH ~7.35) were injected into the Y-channels each at a flow rate of ~0.5 μL/min and duration of ~8 seconds. Under these experimental conditions, the resulting arrays of recording plugs have a ~1:1 (v:v) ratio of aqueous phase and carrier fluid. After recording, the recording plugs from the chemistrode were split into 4 identical daughter arrays in ~100 μm I.D. Teflon tubing for further analysis as discussed below.

Detection of $Ca^{2+}$

The analyzing agent for detecting $Ca^{2+}$ contained ~400 μM cell-impermeant fluo-4 pentapotassium salt, ~400 nM dextran Alexa Fluor® 594, and ~0.1% Tween® 20 in ~25 mM HEPES buffer (pH ~7.35). This solution of reagent was injected into each plug of one daughter array with the average injection ratio of ~0.5 (inject ratio is the ratio between the volume of injected reagent and the volume of the plug before injection). The device used for injection was the same as described in Chen D. L., Li, L., Reyes, S., Adamson, D. N., Ismagilov, R. F., "Using three-phase flow of immiscible liquids to prevent coalescence of plugs in microfluidic channels: Criteria to identify the third liquid and validation with protein crystallization", Langmuir, 23(4), 2255-2260, 2007, the entirety of which is hereby incorporated by reference. Briefly it is a T-junction PDMS device with a hydrophilic glass capillary inserted in the vertical arm of the "T". Reagent solutions were injected into plugs through the hydrophilic glass capillary. The intensities of fluo-4-$Ca^{2+}$ complex, dextran Alexa Fluor® 594, and MPTS in each plug were measured by a DMI6000 Leica fluorescent microscope with GFP, Texas Red, and DAPI filter cube, respectively. MetaMorph 6.0 was used to control the microscope and analyze the data.

To obtain a calibration curve for the concentration of $Ca^{2+}$ in the recording plugs, cartridges of calibration plugs containing solutions were generated. Into each of the calibration plugs was injected the same analyzing reagent used in the analysis of recording plugs, then intensities of fluo-4-$Ca^{2+}$ complex and dextran Alexa Fluor® 594 were detected.

The concentration of $Ca^{2+}$ in the recording plugs was calibrated and corrected following the procedures below:

(i) Calculating the fraction of the analyzing reagent injected:

$$InjectionFraction = \frac{I_{Alexa\ 594, postinjected}}{I_{Alex\ 594, preinjected}}$$

where $I_{Alexa594,\ preinjected}$ is the intensity of Alexa 594 in the analyzing solution before injection, $I_{Alexa594,\ postinjected}$ is the intensity of Alexa 594 in the plugs after injection.

(ii) Correcting the intensity of fluo-4-$Ca^{2+}$ by subtracting the background intensity of the analyzing reagent:

$$I_{Ca2+,corrected} = I_{original,Ca2+} - I_{background,analyzingagent} \times IngectionFraction$$

where $I_{Ca2+,corrected}$ is the corrected intensity of fluo-4-$Ca^{2+}$, $I_{original,\ Ca2+}$ is the original intensity of fluo-4-$Ca^{2+}$ measured from the plugs after injection, $I_{background,\ analyzingagent}$ is the intensity of fluo-4-$Ca^{2+}$ in the analyzing reagent before injection.

(iii) Calculating the final concentration of $Ca^{2+}$ in the calibration plugs after injection:

$$c_{Ca2+,calibration,postinjection} = c_{Ca2+,calibration} \times (1 - InjectionFraction)$$

where $c_{Ca2+,calibration,postinjection}$ is the final concentration of $Ca^{2+}$ in calibration plugs after injection, $c_{Ca2+,calibration}$ is the concentration of $Ca^{2+}$ in calibration plugs before injection.

(iv) By plotting $c_{Ca2+,\ calibration,postinjection}$ versus the corresponding intensity of fluo-4-$Ca^{2+}$, a calibration curve of $Ca^{2+}$ was obtained.

(v) Using the calibration curve and the intensity of fluo-4-$Ca^{2+}$ in the recording plugs, the concentration of $Ca^{2+}$ in each recording plug after injection ($c_{Ca2+,\ sample,\ postinjection}$) was obtained.

(vi) Finally, the concentration of $Ca^{2+}$ in the recording plug before injection ($c_{Ca2+,\ sample}$) was obtained.

$$c_{Ca2+,sample} = \frac{c_{Ca2+,sample,postinjection}}{1 - InjectionFraction}$$

The intensity of MPTS in each could be corrected as well:

$$I_{MPTS,corrected} = \frac{I_{original,MPTS}}{1 - InjectionFraction}$$

where $I_{MPTS}$, corrected is the corrected intensity of MPTS, and $I_{original,\ MPTS}$ is the original measured intensity of MPTS.

Competitive Immunoassay for Insulin Analysis

The labeled human insulin (insulin*) was prepared by reacting human insulin and Alexa Fluor® 488 5-TFP according to manufacturer's instructions. The resulting product was purified by HPLC to obtain a single pure monolabeled isomer (insulin*). The lypholized power of insulin* was dissolved in 1×PBS pH ~7.4 buffer to a concentration of ~40 μM and stored in ~−78° C. freezer as aliquots of ~1 μL. To perform the immunoassay, a reagent solution containing ~72 nM monoclonal anti-insulin antibody (mAb), ~1.2 nM insulin*, ~0.3% BSA and ~0.3% Tween 20 in ~25 mM HEPES was injected into the plugs. The procedure for injecting reagents into plugs was the same as that described for $Ca^{2+}$ detection. The flow rate was ~0.60 μl/min for the plug array and ~0.15 μL/min for the reagent solution. The volumetric ratio of plugs:injected reagent is about 2:1. The insulin and insulin* compete for binding to mAb, thus changing the fraction of free insulin* in the solution. Insulin concentration was inferred by determining the fraction of free insulin* using fluorescence correlation spectroscopy (FCS).

The plugs containing reagents and sample were analyzed by FCS performed on a commercial instrument ConfoCor 3 (Carl Zeiss). A 488 nm Argon laser was used as the excitation light. BP 505-540 IR* was used as the emission filter. For FCS measurements on a plug, the curved carrier fluid-aqueous interface and the thin layer of carrier fluid surrounding the plugs could introduce artifacts. To avoid these potential problems, a cover glass-PDMS device was constructed to house the plug during FCS measurement. The device was fabricated by sealing a piece of PDMS with imprinted channels on the bottom surface to No. 1 cover glass on both its top and bottom surfaces. The bottom cover glass formed an enclosed channel with the PDMS. The two ends of the PDMS channel were connected to 100/150 μm ID/OD Teflon tubing for plugs to move in and out. The center of the channel formed a chamber with dimensions of about 50 μm (height)×150 μm (width)× 350 μm (length). This geometry of the chamber was chosen in order for plugs to become "flat" with minimal curvature of the aqueous-carrier fluid interface and minimal thickness of carrier fluid at the center of the plug's bottom surface. Sealing both the top and bottom of the PDMS piece to cover glass is also preferred to prevent the cover glasses from bending after sealing to PDMS. FCS measurements were performed by focusing the light at the center of the plug and ~25 μm above the cover glass-liquid interface. Control experiments indicated that performing FCS in this geometry does not introduce artifacts due to the aqueous-carrier fluid interface.

The characteristic diffusion time for free insulin* and insulin*-mAb were determined first under the experimental conditions. First, FCS measurements were performed on a solution of the insulin* in the absence of mAb. A single component 3-D free diffusion was used model to fit the autocorrelation curve and obtain the characteristic diffusion time of free insulin*. Next, FCS measurements were done on a series of solutions containing insulin* and increasing concentrations of mAb. The autocorrelation curves were fit using a two-component 3-D free diffusion model, with the diffusion time of free insulin* fixed, to give the characteristic diffusion time of insulin*-mAb complex. In the experiments, the characteristic diffusion time was determined to be ~60 μs and ~230 μs for free insulin* and insulin*-mAb, respectively.

To analyze an array of plugs, the plugs were carefully moved to the PDMS-cover glass chamber using a manual syringe pump. After one plug arrived in the chamber, the flow was stopped and FCS measurements were performed while the plug stayed in the chamber. After the measurement, the next plug was moved into the chamber for measurement and the previous plug was moved out. The autocorrelation curves were fit with a two-component (free insulin* and insulin*-mAb complex) 3-D free diffusion model to give two parameters: the average number of fluorescent insulin* molecules in focal volume and the fraction of insulin* unbound to mAb (free insulin* %). To determine the concentration of insulin, four calibration curves of free insulin* % at different concentrations of insulin were constructed, with average number of insulin* molecules in the focal volume of about 0.65, 0.75, 0.95 and 1.2 respectively.

Detection of Glucose

The analyzing reagent for detecting glucose contained ~0.1 M Girard's reagent T, ~2% acetic acid, and ~20 mM Arabinose. This analyzing solution was injected into each plug of one daughter array of the recording plugs with the average injection ratio of ~0.5 (injection ratio is the ratio between the volume of injected reagent and the volume of the plug before injection). The procedure for injecting reagents into plugs were the same as that described for $Ca^{2+}$ detection. Glucose reacted with the Girard's reagent T (m/z ~132) to form a hydrazone (m/z ~294) resulting in increased detection sensitivity in MALDI-MS.

After incubation under room temperature for ~60 hours, each recording plug was deposited onto the MALDI plate and allowed to evaporate. A matrix solution containing ~10 mg/mL 2,5-dihydroxybenzoic acid in ~1:1 acetonitrile/ethanol was deposited over each sample spot, which was later dried and analyzed by MALDI-MS. MALDI spectra were acquired on an ABI 4700 MALDI TOF/TOF MS instrument, Applied Biosystems. The MALDI plate type was ABI 01-192-6-AB (192 well, Applied Biosystem, 000300011129).

All spectra were obtained with the same instrument settings:
Instrument: 4700 Maldi TOF/TOF MS, Applied Biosystems
Operation mode: MS Reflector Positive
Acquisition control: Automatic
Acquisition mass range: 100-350 Da
Focus mass: 213 Da
Total shots/spectrum: 3000
Fixed laser intensity: 4000 V
Calibration type: default The peak heights in MALDI-MS were measured with Data Explorer™ version 4.8 (Applied Biosystem) software. Level of glucose in each recording plug was presented as the ratio of the peak height of hydrazone of glucose (m/z ~294) to the peak height of Girard's reagent T (m/z~132).

Islets were isolated from pancreata of C57BL/6J wild-type mice (The Jackson Laboratory) ~8-12 weeks of age using collagenase digestion and Ficoll gradients following procedures described in literature. Isolated islets were tranferred to glass bottom culture dishes (Mattek Corporation) and cultured in RPMI-1640 medium supplemented with ~10% fetal bovine serum, ~2 mM L-glutamine, ~100 IU/ml penicillin, and ~100 μg/ml streptomycin. Islets were maintained in a humidified incubator at ~37° C. under an atmosphere of ~95% air/~5% $CO_2$, and were used within ~3 days after isolation.

The experiment to test compatibility of chemistrode with mouse islets is as follows. Islets were loaded with fluo-4 by incubating in Krebs-Ringer buffer (KRB) (~119 mM NaCl, ~4.7 mM KCl, ~2.5 mM $CaCl_2$, ~1.2 mM $MgSO_4$, ~1.5 mM $KH_2PO_4$, ~25 mM HEPES, pH ~7.35) containing ~5 μM cell permeable fluo-4 AM and ~2 mM glucose for ~40 minutes. The MatTek plate containing loaded islets were placed on a DMI6000 Leica fluorescent microscope which was kept at ~37° C. The staining medium was then replaced with KRB containing ~2 mM glucose. A chemistrode was pressed down on the cover glass of the MatTek plate using a micromanipulator to trap one islet in the chemistrode. The PDMS tip of the chemistrode formed a conformal seal with the cover glass to isolate the space in chemistrode from the bulk solution. Plugs of KRB containing either ~2 mM glucose or ~14 mM glucose+~400 nM dextran Alexa Fluor® 594 were formed and transported to the chemistrode. Flow rates: ~0.35 μL/min carrier fluid (~0.5 mg/mL $R_fOEG$ in FC3283), ~0.35 μL/min aqueous stream. Time lapse pictures of the islet under stimulation were taken with the microscope using a GFP filter cube and a Texas Red filter cube every three seconds. The incident excitation light was attenuated with an optical density 2.0 neutral density filter to reduce photodamage to the islet. Pictures were analyzed using MetaMorph 6.0. While data in the GFP channel recorded the $[Ca^{2+}]_i$ response of the islet under stimulation, intensity in the Texas Red channel marked the aqueous solution being applied to the islet (only the high glucose solution contained 400 nM dextran Alexa Fluor® 594).

APPLICATIONS

The chemistrode can be combined with the principle of stochastic confinement. For example, one can stochastically isolate single cells from a mixture of cells into plugs, incubate the plugs to grow clones of the individual cells without competition among different clones, split the plugs into arrays of identical daughter plugs, in which each plug contains clones of the original cell, and analyze each array by an independent technique, including, but not limited to cellulase assays, cultivation, cryo-preservation, Gram staining, and Fluorescence In Situ Hybridization (FISH). Functionally, this approach is equivalent to simultaneously assaying the clonal daughter cells by multiple killing and non-killing methods. For example, a new protocol for single-cell FISH, a killing method, was developed to identify isolated cells of *Paenibacillus curdlanolyticus* (Pc) in one array of daughter plugs using a 16S rRNA probe, Pc196. At the same time, live copies of *P. curdlanolyticus* in another array were obtained for cultivation. A chemistrode that enables sampling of nanoliter volumes directly from environmental specimens, such as soil slurries, has been developed. In addition, a method for analyzing plugs has been developed: an array of plugs is deposited on the surface, and individual plugs are injected into the plugs of the surface array to induce a reaction and enable microscopy without distortions associated with curvature of plugs. The overall approach is useful for identifying rare, slow growing microorganisms and complements current methods to cultivate unculturable microbes from environmental samples.

The combination of a chemistrode and stochastic confinement can be used to isolate individual microbial cells from diverse mixtures into plugs, then incubate these isolated cells to provide growth without competition, and finally split the resulting plugs containing cells into multiple daughter plugs, each containing clones of the original cell. These daughter plugs can then be used for multiple analyses, such as identification and functional testing, in parallel.

Isolation and functional characterization of microbes from diverse multi-species mixtures is of wide interest because these mixtures perform critical functions in environments ranging from soils, to oceans, to niches inside a eukaryotic host. Metagenomic efforts are documenting the genetic diversity of these mixtures, but these methods do not provide access to live cells. Furthermore, short reads do not provide information on which microorganism has which genes. Methods for identifying cells of a specific species within a mixture, for example Fluorescence In Situ Hybridization (FISH), may be used to identify bacteria having particular genes, but FISH is a killing method and does not provide live, isolated microorganisms.

Isolation of microorganisms is difficult because many of them appear to be unculturable in traditional experiments, although new techniques are rapidly improving culturability. One problem with culturing rare cells is that they may grow slowly, and, when grown in a mixture, they get out-competed by other species that grow more rapidly or are present at a higher density initially. Limiting dilution can be used to address this problem: by diluting the original mixture to such an extent that individual aliquots (e.g., 50 μL aliquots placed into wells of a well plate) contain individual cells, competition is eliminated. However, dilution to such a low density makes it more difficult to detect organisms that grow very slowly, undergo just a few divisions, or grow to a low final density. In addition, analysis of secreted molecules, such as cellulase enzymes needed for biomass conversion in the production of biofuels, becomes more difficult when starting with a low density of cells, because secreted molecules are initially present at low concentrations. Finally, such dilution greatly changes the original microenvironment of the sample and may negatively affect the growth of the organism. Gel microdroplets (GMDs) have been used successfully to overcome some of these problems and confine individual cells of microorganisms in small volumes and enhance growth.

In certain embodiments, plugs are aqueous plugs surrounded by an immiscible fluorocarbon carrier fluid, and they are known to be useful for monitoring the growth of cells and for analyzing their secretions. In certain embodiments, the chemistrode relies on multiphase aqueous/fluorous flow to deliver stimuli or to sample responses by trapping a solution into plugs. Separation of competing species into plugs can eliminate competition for nutrients and allows all species to grow. Isolation can also prevent toxic compounds released by one species from contacting the other species. Here, isolating cells in plugs provides several other useful features, including: eliminating scattering from gels, simplifying analysis by microscopy, providing an opportunity to confine and analyze secreted molecules, from the level of a few cells all the way down to the single-cell level, and, after a few divisions of the original cell within a plug, it enables splitting of this plug into daughter plugs, each containing clones of the original cell. This latter feature allows each of the daughter plugs to be manipulated or analyzed by an independent technique. For example, small clonal populations can be analyzed by mutually incompatible techniques, such as those that kill cells and those requiring live cells.

Design and Manipulation of the Chemistrode for Environmental Sampling

A tip of a piece of glass septum theta tubing (~1.5 mm, World Precision Instruments) was made sharp by fusing, and then inserted into a piece of Tygon tubing (~250 μm I. D., ~2000 μm O. D.). Then a piece of a standard, polyimide coated, flexible, fused silica capillary (~318 μm I. D., ~435 μm O. D., Polymicro) was inserted into the other end of the piece of Tygon tubing. A piece of Teflon tubing (~100 μm I. D., ~150 μm O. D., Zeus) was inserted into the open end of the glass septum theta tubing, through the Tygon tubing, all the way down to the distal tip of the silica capillary. A second piece of Teflon tubing (~200 μm I. D., ~250 μm O. D., Zeus) was also inserted into the open end of the glass tubing, and this tubing extended only down to the proximal tip of the glass tubing. The gap between the two pieces of Teflon tubing and the glass tubing was filled with half-cured polydimethylsiloxane (PDMS) glue (Dow-Corning Sylgard 184 A and B at a ratio of ~10:1, cured at ~110° C. for ~110 s), and then the device was baked at ~65° C. for the PDMS glue to fully cure.

For sampling, the chemistrode was held by the Tygon tubing, and the tip was dipped into the aqueous sample. The carrier fluid was delivered from the 200 μm I. D. Teflon tubing at ~0.5 μL min$^{-1}$, and it flowed to the tip of the chemistrode through the space between the silica capillary and the Teflon tubing. A negative pressure was applied on the longer piece of Teflon tubing (~100 μm I.D.) by aspirating at ~0.9 μL, min-1. Both the carrier fluid and the aqueous sample were aspirated into this Teflon tubing, and the aqueous sample was segmented into plugs by the carrier fluid at the entrance.

Cultivation of Microorganisms and Culture Media

Bacterial species of *Paenibacillus curdlanolyticus* (*P. curdlanolyticus*, ATCC 51899) and *Escherichia coli* (*E. coli*, ATCC 25922) were obtained from the American Type Culture Collection. *P. curdlanolyticus* cells were enriched in ~30 g/L of sterilized trypticase soy broth (TSB) media (BD Company) at ~30° C. for 12 h, and *E. coli* cells were enriched in Difco Luria-Bertani (LB) broth media (BD Company) at ~37° C. for ~3 h. Seed inoculum of each species was cultured in a rotary shaking incubator (SI-600 Lab Companion, Jeio Tech) at ~180 rpm. During the seed culture of *P. curdlanolyticus* species, cellulases were induced by adding filter-sterilized (~0.45 μm, Whatman) carboxymethyl-cellulose (CM-cellulose; sodium salt, 0.7 D.S., Sigma-Aldrich) at ~1 g/L final concentration.

The green fluorescence protein (GFP)-labeled *E. coli* (a mutant *E. coli* strain containing PUCP24/EGFP plasmids in *E. coli* K12 YMel-1 host) was constructed in the laboratory. The red fluorescence protein (RFP)-labeled *E. coli* (a mutant *E. coli* strain containing DsRed encoding plasmids in *E. coli* DH10B host) was provided by Professor Benjamin Glick of the University of Chicago. GFP-labeled *E. coli* was cultured in Difco tryptic soy agar (TSA) media (BD Company) that included ~100 mg/L kanamycin and ~20 mg/L gentamicin. RFP-labeled *E. coli* was cultured in TSA media that included ~100 mg/L ampicillin.

Preparation of Live Cells

An inoculum of either *P. curdlanolyticus* or *E. coli* was cultured in either TSB (for *P. curdlanolyticus*) or LB (for *E. coli*) media respectively. Seed inoculum of either GFP-labeled *E. coli* or RFP-labeled *E. coli* was cultured in either LB media including ~100 mg/L kanamycin (for GFP-labeled K coli) or LB media including ~100 mg/L ampicillin (for RFP-labeled *E. coli*) respectively. Cells in a seed culture were harvested at the exponential phase, and then the cells were washed twice with autoclaved ~0.9% (w/v) NaCl solution. For immediate use, the number of live cells for each species was approximately estimated by either counting cells under an epi-fluorescence microscope (DMI 6000 B, Leica) (for GFP-labeled *E. coli* and RFP-labeled *E. coli*), or by staining with live/dead fluorescent dye (Live/Dead BacLight Bacterial viability kit, Molecular Probes) then counting cells (for *P. curdlanolyticus* and *E. coli*), or by measuring optical density through a UV/Vis spectrophotometer (Agilent) for *P. curdlanolyticus* and *E. coli*. The number of live cells of each species was determined by the colony counting method in agar plates.

Mixed Culture of *P. Curdlanolyticus* and *E. Coli* in an Agar Plate

After each cell suspension was serially diluted with sterilized NaCl solution (~0.9%, w/v) down to a cell density of ~$10^1$ CFU/mL, cell suspensions of *P. curdlanolyticus* and *E. coli* were mixed to form suspensions with different density ratios. The cell density of *E. coli* was kept at approximately ~$10^4$ CFU mL$^{-1}$, and the cell density of *P. curdlanolyticus* was either about $10^4$, $10^3$, or $10^2$ CFU mL$^{-1}$. Then the mixtures with different ratios were respectively spread on TSA plates, and incubated at ~30° C. for ~36 h. Based on the different morphology, colonies of either *P. curdlanolyticus* or *E. coli* were distinguished visually.

Isolation of Bacterial Cells in Plugs by Stochastic Confinement and Incubation of the Plugs Plugs, approximately 10 nL in volume, were formed by using the method described previously. Briefly, the plugs were formed in a three-inlet PDMS device with ~100 μm wide channels by flowing the cell suspension diluted with TSB at approximately 5×~$10^4$ CFU mL$^{-1}$ at ~0.4 μL min$^{-1}$ and the fluorinated carrier fluid (FC40 containing ~0.5 mg/mL R$_f$OEG) at 0.5 μL min$^{-1}$. A long spacer of carrier fluid was introduced via the third inlet after every ~30 plugs were formed. Plugs were collected into ~200 μm I. D. Teflon tubing, which was inserted into the device up to the inlet junction and sealed in place with wax (Hampton Research). After formation of plugs, the tubing was disconnected from the PDMS device, and the ends of the tubing were sealed with wax. Then, the tubing was incubated in a Petri dish containing ~0.5 mL of TSB media at ~30° C. To maintain sterility, all tubing, devices, and syringes used were sterilized by using ~70% (v/v) ethanol, and all solutions and media used were either autoclaved or filtered through ~0.45 μm PES or PTFE filter.

Splitting Plugs

Each individual plug was split into four daughter plugs by two steps of two-way splitting via methods described in D. Chen, W. B. Du, Y. Liu, W. S. Liu, A. Kuznetsov, F. E. Mendez, L. H. Philipson and R. F. Ismagilov, Proc. Natl. Acad. Sci. U.S.A., 2008, 105, 16843-16848; and D. N. Adamson, D. Mustafi, J. X. J. Zhang, B. Zheng and R. F. Ismagilov, Lab Chip, 2006, 6, 1178-1186, the entireties of which are hereby incorporated by reference. As the plugs moved through the tubing towards the junction, each plug was split into two daughter plugs, and each of these daughter plugs was also split. In other words, four identical daughter plugs were split off from each incoming plug. The daughter plugs resulting from a particular splitting event were collected into four separate segments of ~100 μm I. D. Teflon tubing, for a total of four arrays of daughter plugs. After splitting, the plugs in each daughter array were recognized as copies of the initial incoming plugs, and the cells in the initial plugs had been distributed among the daughter plugs. The order of the daughter plugs in each array corresponded to the original order of the incoming plugs from which they were generated.

Cellulase Assay on Bacteria in an Array of Plugs

The synthetic substrate resorufin cellobioside (Marker-Gene fluorescent cellulase assay kit, MGT Inc.) was used to measure the cellulolytic activity of either *P. curdlanolyticus* or *E. coli* in culture broth. The stock solution of resorufin cellobioside (~5 mM) in DMSO was diluted by the reaction buffer (~100 mM sodium acetate, pH ~6) into ~0.5 mM resorufin cellobioside solution. This resorufin cellobioside solution was then injected into each plug in an array by using a PDMS T-junction with a volumetric ratio of ~1:1. After disconnecting the tubing containing the plugs from the PDMS device and then incubating the tubing at room temperature for ~8 h, each plug was imaged. A high intensity of red fluorescence indicated that the fluorogenic substrate of resorufin cellobioside was cleaved by the cellulolytic enzymes produced by *P. curdlanolyticus*, whereas lower intensity levels of fluorescence indicated either empty plugs or plugs containing non-cellylolytic species, i.e. *E. coli*.

Plate Culture of Bacteria in an Array of Plugs

To culture each plug containing either *E. coli* t or *P. curdlanolyticus*, plugs were deposited ~0.5 cm apart onto a TSA plate using a micro-aspirator (Stoelting) under a stereomicroscope (SMZ-2E, Nikon). One spot on a TSA plate corresponded to a single plug. Deposition of plugs was guided by an Easigrid colony template (Jencons) attached on the bottom of a plate. After deposition of plugs, the plate was then incubated at ~30° C. overnight. Growth of colonies of either *P. curdlanolyticus* or *E. coli* indicated the presence of that species in the corresponding plug.

Cryo-Preservation of Bacteria in an Array of Plugs

For the long-term preservation of plugs, an autoclaved ~40% (v/v) glycerol stock solution was injected into each plug in an array by using a T-junction with a volumetric ratio of ~1:1, so that the final concentration of glycerol in each plug was ~20% (v/v). The tubing containing plugs was frozen rapidly by being placed in liquid nitrogen, and then the tubing was stored in a deep freezer at ~−80° C. After the frozen tubing was aseptically thawed on a clean bench at room temperature, each plug was transferred onto the surface of a TSA plate using a micro-aspirator (Stoelting) under a stereomicroscope (SMZ-2E, Nikon), and then the plate was incubated at ~30° C. overnight to revive cells.

Gram Staining of Bacteria in an Array of Plugs

The LIVE BacLight bacteria Gram stain kit (Molecular Probes) was used to stain the bacteria. The staining solution was prepared by adding ~1.5 μL of 3.34 mM SYTO9 (a green fluorescent dye that stains both live, Gram-positive and live, Gram-negative bacteria) in DMSO and ~1.5 μL of ~4.67 mM hexidium iodide (a red fluorescent dye that preferentially stains live, Gram-positive bacteria) in DMSO to ~1 mL of filter-sterilized water. An array of plugs of the staining solution, each plug approximately 60 nL in volume, was prepared by spotting the staining solution on a piece of cover slide immersed in FC40 by using ~300 μm I. D. Teflon tubing (Weico Wire & Cable). Plugs, contained in ~100 μm I. D. Teflon tubing, were then deposited onto the cover slide; each plug was deposited into one plug of staining solution. Bacteria in each plug were then imaged. Green fluorescence indicated Gram-negative, live *E. coli* cells, whereas red fluorescence indicated Gram-positive, live *P. curdlanolyticus* cells.

Fluorescence In Situ Hybridization (Fish) of Bacteria in an Array of Plugs

A 16S ribosomal-RNA targeted probe specific to *P. curdlanolyticus* (Pc196) was designed by Ribocon GmbH and constructed by and purchased from biomers.net—the biopolymer factory (Ulm, Germany) (sequence: 5'-gaa aga ttg etc ctt ctt-3' conjugated to the fluorophore Atto550 at the 5' end). A new protocol for the detection of *P. curdlanolyticus* was developed, and optimal hybridization conditions for the probe were determined using *P. curdlanolyticus* that had been cultured in bulk in TSB media and then fixed while the *P. curdlanolyticus* cells were in the early stages of exponential growth. The solution for fixing the cells consisted of ~50% cold ethanol (~4° C.) and ~50% RNase-free 1×PBS (~145 mM NaCl, ~1.4 mM $NaH_2PO_4$, 8 mM $Na_2HPO_4$, in RNase-free water (Thermo Scientific), pH ~7.4). The *P. curdlanolyticus* cells in fixative were then stored at ~−20° C. for ~20 h. The fixation procedure for detection of *P. curdlanolyticus* in bulk was modified as follows to detect *P. curdlanolyticus* isolated in plugs. For fixation after stochastic confinement, plugs containing bacteria grown in TSB media were merged with a stream of ~100% ethanol by using a T-junction with a volumetric ratio of ~1:1. The resulting plugs of ~50% ethanol and ~50% TSB media were incubated at ~−20° C. for ~20 h. After fixation, plugs containing fixed bacteria were spotted on UltraStick glass slides (Gold Seal). While most bacteria adhere to the UltraStick glass slides, to prevent any potential cross contamination of isolated bacterial species between spotted plugs, a PDMS membrane containing ~5% carbon and ten ~5 cm wells was sealed to the UltraStick slides, and one plug was spotted in each well. Prior to hybridization, the hybridization buffer (~900 mM NaCl, ~20 mM Tris/HCl, ~20% formamide, ~0.1% SDS, and ~5 ng/µL Pc196 in RNase-free water) was pre-warmed at ~48° C. For hybridization, ~100 µL of the buffer was added to each well containing a plug of isolated bacteria. Bacteria were incubated in the hybridization solution for ~two and a half hours at ~48° C. The hybridization solution was then removed, and bacteria were washed for ~30 minutes with washing solution (~56 mM NaCl, ~20 mM Tris/HCL, ~5 mM EDTA, ~0.01% SDS in RNase-free water) at ~48° C., and next washed at room temperature with 1×PBS buffer (pH ~7.4). Following hybridization, each spot corresponding to a cataloged plug was scanned using a VT Infinity 2-D array scanner confocal system with an array of ~50 µm pinholes (Visitron Systems, Germany) coupled to a Leica DMI6000 inverted microscope (Leica Microsystems, Germany) and a ~568 nm±2 nm diode laser (exposure time ~800 ms, gain 180). Images were obtained with a back-thinned electron multiplier CCD camera (16 bit, 512×512 pixels) (Hamamatsu Photonics, Japan) and an 20×0.7 NA objective using Simple PCI software (Hamamatsu Corporation, Japan). All stained bacteria were kept in 50% DABCO during imaging to prevent photobleaching. Intensities of imaged *P. curdlanolyticus* and *E. coli* were compared to ensure reliable identification of *P. curdlanolyticus*, and the intensities were analyzed using MetaMorph Imaging System (Molecular Devices). A linescan with a scan-width of one pixel was taken across the bacteria. Data presented is of the intensity along the linescan minus 200 a.u. of background scattering. Images were processed using Adobe PhotoShop 6.0.

The combination of a chemistrode and stochastic confinement can be used to study environmental microbiology and the human microbiome. Some microbes in these environments are "unculturable" via traditional plate-based methods. It is thought that the media used in these traditional methods may selectively enrich certain species in the environmental sample, allowing them to out-compete other species. The losing species in this competitive interaction are not recovered from plates and therefore deemed "unculturable". However, it may be the case that the growth of these "unculturable" species strongly relies on their original media, which may contain specific amounts of certain materials or molecules which are required for growth. Without being bound by theory, culturing these "unculturable" microbes may require using the original sample from the environment, and then incubating the cells in the original media, rather than on plates. One of the challenges of using the original sample from the environment is that samples from some environments—such as soil, sediments, blood, and the human gut—may adhere to and foul or occlude sampling devices.

Plugs can be used to transport solids reliably, including suspensions of inorganic nanoparticles, protein microcrystals, agglutinated red blood cells, and clotted blood. To sample microbes directly from their environment, in their original media, and without fouling of the device, a modified chemistrode can be used to form plugs immediately as the sample flows into the tip. This modified chemistrode has been used to sample soil slurry. The modified chemistrode consisted of a piece of hydrophilic silica capillary with a piece of hydrophobic Teflon tubing inserted inside. The carrier fluid was delivered to the tip of the probe through the space between the silica capillary and the Teflon tubing. Aspiration at a flow rate higher than the flow rate at which the carrier is delivered removed both the carrier fluid and the aqueous sample into the Teflon tubing, and the aqueous stream was segmented into plugs by the carrier fluid at the entrance of the Teflon tubing. The carrier fluid was contained inside the chemistrode by capillary forces that keep the carrier fluid adherent to the Teflon walls.

Having demonstrated that the modified chemistrode can successfully sample directly from the environment, rest of the approach was then tested by forming plugs using a device similar to the one that was previously used for stochastic confinement (J. Q. Boedicker, L. Li, T. R. Kline and R. F. Ismagilov, Lab Chip, 2008, 8, 1265-1272, the entirety of which is hereby incorporated by reference). With a mixture of two fluorescence-labeled strains of *E. coli*: GFP-labeled *E. coli* and RFP-labeled *E. coli* in equal proportions, the principle of stochastic confinement was then used to isolate single bacterial cells into individual plugs. When the number of plugs generated was much higher than the number of cells present initially, among those plugs containing cells, most contained only cells of GFP-labeled *E. coli* or only cells of RFP-labeled *E. coli*. The statistical property of this process can be described by the Poisson distribution. It is known in the art that encapsulation of cells in plugs does not introduce artifacts to cell growth, and it was confirmed that single cells, isolated in plugs and incubated, formed populations with growth rates similar to those observed for cells in bulk solution.

After incubation of the plugs to allow time for a few divisions of the original cell within a plug, each of the plugs in the original array was split to create four identical, parallel daughter arrays. There was no cross-contamination between plugs during the splitting, because the plugs were well separated from each other, as well as from the surfaces of the tubing and the PDMS devices, by the carrier fluid. The statistical probability of the resultant distribution of cells in the four daughter plugs, assuming that all cells in each initial plug had an equal probability of being distributed into each of the daughter plugs, can be calculated. After five cycles of divisions from a single cell (i.e., when there are ~32 cells in a plug), there is greater than ~99% probability of having at least one cell in each daughter plug. It is possible that cells of some bacterial species would form clusters and not split evenly among the daughter plugs. It was experimentally confirmed that gentle shear in the plugs (average shear rate ~60 s-1) was sufficient to break up any clusters of all strains of *E. coli* or *Paenibacillus curdlanolyticus* used. Thus, splitting reliably generates parallel copies of the bacterial populations for multiple tests.

The chemistrode combined with stochastic confinement can be used to (a) isolate individual cells in a multi-species mixture by stochastically encapsulating the cells in an array of individual plugs, (b) incubate the plugs to grow colonies of the isolated cells without cross-species interference, (c) split the plugs into arrays of identical daughter plugs to perform multiple tests in parallel, such as identification and functional tests. To demonstrate, individual bacterial cells of either GFP-labeled *E. coli* or RFP-labeled *E. coli* were stochastically isolated from a mixture of both *E. coli* t strains into plugs. Incubation of the plugs enabled these isolated single bacterial cells to grow. These plugs were incubated for six hours after formation, and the bacterial cell in each individual plug (if present) divided and grew. After incubation, each plug was split into four identical daughter arrays.

The same approach can be used to do the same for cells of a rare species in a multi-species mixture. In this context, *Paenibacillus curdlanolyticus* was chosen as the rare, relatively slow-growing species, and wild-type *E. coli* was chosen as the abundant, rapidly-growing species. *P. curdlanolyticus* cells produce and secrete cellulolytic enzymes, a class of enzymes interesting for conversion of biomass into biofuels; whereas, the *E. coli* species used does not produce any similar enzymes to cleave cellulose.

Mixtures of *E. coli* and *P. curdlanolyticus* were prepared at different ratios of viable cell numbers—about 1.5:1, 2:1, 15:1, 20:1, and 200:1—and suspensions of these mixtures were spread on TSA plates. *P. curdlanolyticus* colonies were detected visually, based on differences in morphology of colonies, in plates spread with suspensions of the mixture with the ratio of either about 1.5:1 or 2:1. *P. curdlanolyticus* colonies were not detected in plates with the ratio of about 15:1, 20:1 and 200:1, indicating that *E. coli* was out-competing *P. curdlanolyticus* on the TSA plates. This result confirms the known difficulty of isolating rare species present at low abundance using conventional plating methods. Here, when the ratio of *E. coli* to *P. curdlanolyticus* was above ~15:1, no cells of the rare species were recovered.

The cells in the mixture were then isolated into individual plugs and the cells of *E. coli* and *P. curdlanolyticus* were incubated in plugs. *P. curdlanolyticus* cells that successfully grew up to hundreds of cells could be recovered in all cases, from ratios of about 1:1 to 40:1. This observation is consistent with the individual species separating into different plugs so that the slow-growing species (i.e., the *P. curdlanolyticus* strain) can have an opportunity to grow without any competition with the fast-growing species (i.e., the *E. coli* strain). The fraction of the recovered *P. curdlanolyticus* was always lower than ~100%, because there is a minor probability that both a *P. curdlanolyticus* cell and an *E. coli* cell are isolated together in some plugs, according to the Poisson distribution. In such a case, the *E. coli* cells would dominate the growth in those plugs, and the *P. curdlanolyticus* cells in those plugs could not be recovered. The fraction of *P. curdlanolyticus* cells that were recovered was variable among different experiments, presumably because of the stochasticity of the isolation of cells into plugs.

The culturing method of "dilution to extinction" also uses the principle of stochastic isolation. However, in these methods there is a very low starting concentration of the inoculum (~10° CFU/mL). On the other hand, encapsulating a single bacterium in a plug with a volume of ~10 mL provides a cell density of ~$10^5$/mL in a single plug. Increasing the inoculum density (e.g., to ~$10^5$ CFU/mL) allows a dramatic reduction in the culturing time required to reach detectable cell densities. Creating high inoculum density by isolating individual bacterial cells in plugs is especially important for those bacterial species that have slower division rate at lower concentration, because the rapid accumulation of the molecules or enzymes in the confined environment of the plug may enhance growth of cells. Furthermore, plugs require much lower volumes of reagents for the isolation and the cultivation of bacterial samples. Thus, plug-based methods that rely on stochastic isolation have many advantages over the culturing method of "dilution to extinction".

Methods with gel microdroplets (GMDs) also use stochastic confinement to isolate single cells, and isolation by GMDs may be useful for separating and culturing symbiotic species, as compounds can diffuse between GMDs. However, using plugs allows splitting of the plugs to form identical copies for analyses with multiple techniques in parallel.

Rare individual cells in a mixture were isolated by stochastic confinement at ratios much lower than those that were achievable using plate-based methods. Colonies of both *E. coli* and *P. curdlanolyticus* were observed after spreading a mixture of *E. coli* and *P. curdlanolyticus* cells, with the ratio of cell density at ~1.5:1, onto a TSA plate and incubating the plate for ~36 h. Colonies of only *E. coli* cells were observed after spreading a mixture of *E. coli* and *P. curdlanolyticus* cells, with the ratio of cell density at ~15:1, onto a TSA plate and incubating the plate for ~36 h. No *P. curdlanolyticus* colonies were observed after ~36 h. See also, Weishan Liu, Hyun Jung Kim, Elena M. Lucchetta, Wenbin Du, and Rustem F. Ismagilov, "Isolation, incubation, and parallel functional testing and identification by FISH of rare microbial single-copy cells from multi-species mixtures using the combination of chemistrode and stochastic confinement", Lab Chip 2009 online DOI: 10.1039/b904958d, the entirety of which is hereby incorporated by reference.

These methods can be combined with splitting to create parallel arrays for further testing. Staring with a mixture of *E. coli* and *P. curdlanolyticus* at a concentration ratio of ~40:1 does not result in recovery of *P. curdlanolyticus* colonies when the mixture is spread on plates. After isolation and incubation in approximately 1000 plugs, 100 plugs were split into four daughter arrays. Each daughter array also contained 100 plugs, all of which were copies of the original plugs. Each array of plugs was then used to perform one of four different tests.

Populations grown from the isolated single cells were split for parallel tests. Individual cells in a mixture of *E. coli* and *P. curdlanolyticus* (ratio of cell density, ~40:1) were isolated stochastically in plugs and incubated. Then the plugs were split into four daughter arrays which were used for (a) a cellulase assay, (b) cultivation, (c) cryo-preservation, and (d) Gram staining, respectively.

The first daughter array of plugs was used for the cellulase assay. Fluorescence in each plug was detected after each plug was injected with a solution of the fluorogenic substrate resorufin cellobiosides and incubated at room temperature for ~8 h. Plugs containing *P. curdlanolyticus* showed more than two times higher fluorescence than plugs containing *E. coli*, and more than four times higher fluorescence than empty plugs. Injection of reagents into plugs is known in the art. Plugs in the second daughter array were deposited onto a fresh TSA plate, and then incubated at ~30° C. for ~20 h to grow individual colonies. It was confirmed that pure colonies of either *P. curdlanolyticus* or *E. coli* grew on the surface of the TSA plate where the corresponding plugs containing either *P. curdlanolyticus* or *E. coli* were deposited. Plugs in the third daughter array were used for cryo-preservation. After injection of glycerol, the plugs were frozen by using liquid nitrogen, and then they were stored at ~80° C. for ~one day. To test the recovery of the viability of the cells in the cryo-preserved plugs, those plugs were thawed on the second day and deposited onto a fresh TSA plate for incubation. Colonies grew on all the locations on the surface of the TSA plate where plugs containing cells were deposited. The fourth daughter array of plugs was used for Gram staining. It was confirmed that the Gram-positive *P. curdlanolyticus* species was stained in red, and the Gram-negative *E. coli* species was stained in green by the fluorescent dye used here.

A new method for analyzing plugs was developed: an array of plugs is deposited onto a surface, and individual plugs are injected into the droplets of the surface array to induce a reaction. This method was then used to perform Gram staining of cells in plugs. After immersing a piece of glass slide in fluorocarbon, an array of aqueous droplets of the reagent for analysis (Gram staining solution) was first generated on the slide surface. Next, each plug in the tubing was deposited into one droplet of reagent, and due to surface tension, the plugs and the droplets merged reliably. Readout of reactions in the droplets was imaged optically from the bottom of the slide. Because there was no curved surface in the light pathway, aberrations common in imaging of plugs in tubing were eliminated. Two common problems of injecting reagents into plugs by using a PDMS T-junction are that the volumetric injection ratio is limited, and that many compounds in the reagents tend to be adsorbed on the PDMS surface. This method circumvents these problems while still enabling high throughput analysis. Moreover, immersion in fluorocarbon minimizes the evaporation of the droplets and enables long reaction times (e.g. days). This method can be generally used for analyzing the contents of plugs.

Using the combination of a chemistrode with stochastic confinement and splitting of the plugs not only enables performing multiple parallel tests immediately after incubation of the cells in the plugs, but also enables tracing each plug in a daughter array back to the initial plug from which it was split. Because the order of the original plugs is preserved in the order of the daughter plugs, plugs in parallel daughter arrays can be traced by encoding patterns in the sequence of plugs when they are formed. For example, a long carrier fluid spacing was introduced between every 30 plugs for the identification of sequences of plugs. By tracing the sequences of plugs, the order of the four different plugs in the four different arrays that were used for four different tests was matched. Thus, the four arrays could be reliably aligned, and any potential errors in the alignment, such as might occur if a plug were to split or two plugs were to coalesce, would not propagate. On one hand, rapid classification or identification tests can locate particular plugs containing cells of interest in the array, so that these plugs can be collected for culture. On the other hand, the ability to preserve viable cells in plugs allows for culturing cells long after the splitting event and after knowing the results of a parallel identification test on another daughter array. The splitting also enables the use of incompatible techniques on identical copies of cell populations from the same original single cell. For example, identification techniques such as DNA sequencing and FISH require killing of the cells, while live cells are required for cultivation and functional tests as the cellulase assay.

Gram-staining was performed on a glass slide immersed in fluorocarbon. (a) A two-dimensional array of droplets of the staining solution for the Gram test, a mixture of SYTO 9 and hexidium iodide, was first spotted onto a piece of glass slide immersed in fluorocarbon (FC-40). (b) The plugs for the test were then deposited into the droplets of the staining solution. One plug was deposited into each droplet of the staining solution. (c) The fluorescence of the stained cells in each droplet was observed from the bottom of the slide by using an epi-fluorescence microscope. The slide was immersed in FC-40 during the whole process so that there was no significant evaporation of aqueous droplets.

It was shown that Fluorescence In Situ Hybridization (FISH) can be used to identify *P. curdlanolyticus* cells in one of the identical daughter arrays while using the cells in another daughter array for cultivation. A protocol to detect *P. curdlanolyticus* in bulk was developed and then modified to detect *P. curdlanolyticus* isolated in plugs. After isolating and incubating a mixture of *P. curdlanolyticus* and *E. coli* with a concentration ratio of ~1:1 in approximately 200 plugs, all plugs were split into four identical daughter arrays. Cells in plugs from the first daughter array were fixed by injecting ~100% ethanol into each plug using a T-junction, resulting in ~50% ethanol and ~50% TSB media (v/v) in each of the plugs. Then the plugs were stored at ~20° C. for ~20 hours and fixation took place. After fixation, ten plugs were spotted into wells of a PDMS membrane sealed to an UltraStick glass slide. Following staining with a 16S ribosomal RNA probe specific to *P. curdlanolyticus* (Pc196), one first plug was identified as containing *P. curdlanolyticus* based on the fluorescence observed. A second plug was identified as containing a different species (*E. coli*), judging by weak non-specific fluorescence. A third plug was found to be a blank plug, as no fluorescence was observed. Using this protocol, the fluorescence intensity of *P. curdlanolyticus* stained with the Pc196 probe was ~9000 a.u. above background, and fluorescence of *E. coli* stained with the same probe was ~100 a.u. above background. This ~90:1 ratio of intensities facilitated the identification of *P. curdlanolyticus*. Fluorescence intensity was similar to that of controls where the procedure was performed in bulk (i.e. outside of plugs), indicating that FISH staining from plugs can be performed without loss of staining quality. Plugs in the second daughter array were spotted and cultured on a culture plate. Colonies of *P. curdlanolyticus* also grew at the location of a plug in the second daughter array corresponding to the first plug in the first daughter array that was found to contain *P. curdlanolyticus* based on the FISH measurement.

Parallel live cultivation and killing identification by Flourescence In Situ Hybridization were performed on clones of the same cell. FISH was used to identify *P. curdlanolyticus* cells in one of the identical daughter arrays while using the cells in another daughter array for cultivation. After splitting an array of plugs into daughter arrays, one daughter array of plugs were fixed FISH by injection of ethanol into each plug using a T-junction. A PDMS membrane containing ~5% carbon with holes was attached onto an UltraStick glass slide to form staining wells for FISH, into which the plugs containing fixed cells were then deposited. Ten plugs in a daughter array were deposited and stained by FISH using the probe Pc196. *P. curdlanolyticus* cells contained in a plug were identified. Other plugs were found to be blanks or contain *E. coli*. A second, parallel array of daughter plugs was used for cultivation. A colony of *P. curdlanolyticus* grew after culturing a plug from the second array that corresponded to the plug in the first array found to contain *P. curdlanolyticus* by FISH.

Plug-based microfluidic approaches can be used to accomplish a set of single-cell microbiologic processing: from sampling directly from an environment, to isolating single cells from a multi-species mixture, to identifying cells of interest by killing methods while at the same time providing their clonal copies for functional testing, culturing, or preservation. Sampling directly from the environment with high spatial resolution, as provided by the chemistrode, is attractive for understanding spatial structures present in natural and synthetic microbial communities.

It is preferred that isolated cells are culturable individually in plugs, and thus is preferred for working with any cells that do not require symbiotic microorganisms for growth, and it is especially useful for attaining rare species in mixtures that are dominated by competitive interactions.

This embodiment of the chemistrode can be used for culturing isolated cells in their original media, which may contain compounds required for growth. Even if the initial growth in plugs is minimal (just a few divisions), FISH can be used to identify species of interest. After identification, alternative techniques and conditions can be used to successfully culture the sample of the species preserved in the parallel array. For example, the hybrid method (L. Li, D. Mustafi, Q. Fu, V. Tereshko, D. L. L. Chen, J. D. Tice and R. F. Ismagilov, Proc. Natl. Acad. Sci. U.S.A., 2006, 103, 19243-19248; the entirety of which is hereby incorporated by reference) could be used to generate large numbers of different conditions in plugs to screen optimal growth condition.

This microfluidic approach described is useful for studies in environmental microbiology and of the human microbiome or for diagnostics. It is applicable to other cells in addition to bacteria. For example, it may be used to propagate and analyze immune cells after isolation from patients. The integration of FISH for identification of rare bacterial species with stochastic confinement using *P. curdlanolyticus* as the rare species has been demonstrated. This approach can also be used for the detection of other microbes or cells in single or low numbers, including archae, gram-positive bacteria, gram-negative bacteria, or mammalian cells as is performed in prenatal and cancer diagnostics. This approach complements current methods for FISH detection.

Applications of the chemistrode include collecting diagnostics and sampling such as blood collection with rapid anticoagulation (optionally with many different anticoagulants, like heparin and EDTA), analysis of interstitial fluid, immune testing for autoimmune diseases and allergies, cerebrospinal fluid testing including diagnosis of Alzheimer's disease and monitoring metabolic activity of the central nervous system. Sampling CSF and/or ISF can be used in the diagnosis of Alzheimer's disease and other neuron degenerative diseases, for monitoring metabolic activity of the central nervous system, osteogenesis, tumor progression and development, and pharmacokinetics. Molecules that can be collected in ISF include, but are not limited to, soluble signaling molecules that are secreted by cells into the ECM (extracellular matrix), including cytokines, chemokines, reactive oxygen species, enzymes that cells secrete to alter the ECM, such as matrix metalloproteases, fragments of ECM proteins, collagen pro-peptides, a by-product of collagen fibril assembly, collagen break-down products, a sign of turnover of the ECM, which increase during tumor evolution. A chemistrode can be inserted intravenously for continuous sampling. It can be inserted using an Infusaport. It can be applied to humans, animals or plants. It can be used to sample body fluid and archived samples. It can be coupled to electronic systems to give immediate readouts of diagnostically relevant components. It can be coupled to electronic systems for later retrieval of data by physicians. It can be used for delivering chemicals to the environment and at the same time record the chemical response of the environment in plugs.

The chemistrode may be used for sampling and storing of samples. Once samples are collected as plugs they may be frozen and stored. The plugs can then be thawed and analyzed later. The chemistrode may also be used to develop a platform for long-term storage and bio-banking (rapid freezing and manipulation) of many samples, or many aliquots of the same sample, in an easily accessible form, where aliquots of sample can be retrieved without having to thaw the entire sample. In this platform, samples are segmented and stored into plugs of very small volume. The frozen samples are bathed in an immiscible carrier fluid (fluorocarbons or freons) that is liquid at the temperature of storage or manipulation. The advantage of this method is that while the samples can be stored frozen, the carrier fluid may remain liquid, and therefore frozen samples may be manipulated without thawing. Alternatively, this manipulation may be accomplished by storing under even lower temperature, but for retrieval raising the temperature above the freezing temperature of the carrier fluid while still below the freezing temperature of the samples. Samples can be retrieved either sequentially or in a random access mode, by pushing the frozen plugs out of the end of the storage tube into a receptacle, or push them past a T-junction after which a stream of carrier can be used to push it further. Manipulation can be in 1D, 2D or 3D arrays using pressure, magnetic, electrostatic, optical, and other forces. Optionally indexing methods such as using internal markers or external markers can be used to identify individual samples if needed.

Samples which may be collected by the chemistrode and stored in plugs include blood from capillaries or interstitial fluid or cerebral spinal fluid. Samples may be collected over time and stored (for example to determine whether different chemicals are found in the environment over time, or to determine if pulses of a chemical are present). Samples may be collected from different spatial positions of the environment. This can be done by moving a single device in space during sampling, or using an array of sampling devices. A chemistrode can be used in situations where the environment produces only small amounts of material, or when it is desirable to remove only a small amount of material to minimize perturbing the system. Examples of such situations include the collection of cerebral spinal fluid or interstitial fluid.

The chemistrode may be used for process control or sample collection for archiving and analysis. The process being sampled by the chemistrode could be, for example, in a reactor, a flow reactor, a batch reactor, or in a separation system like a chromatography system. Examples include sampling compounds from plates for thin-layer chromatography and delivery to analysis, for example, by mass-spectrometry. In addition, biomolecules may be sampled from a separation gel, such as a 1D or 2D electrophoresis gel. For example a process for making pharmaceuticals could require keeping samples on record to prove that the process was not contaminated or flawed. Chemistrode sampling and storage could be applied to a process that happens too quickly to analyze immediately so one could sample, store and analyze later. Chemistrode sampling and storage can also be applied to processes that happen on a small scale and are difficult to monitor. Chemistrode sampling and storage can be used for the collection of interfering chemicals such as when collecting cells, where microbes are interfering. Using the device, one could selectively pick up a small volume which contains the interfering microbe. Chemistrode sampling and storage can be applied to a suspension of particles and/or cells, such as in environmental monitoring where the sample may be a soil suspension or mud. The chemistrode can be applied to humans and animals, cells such as islet cells, stem cells, a surface that is clotting, animal models (e.g., singing birds, rodents, or zebra finches), sperm cells, egg cells, mast cells, bacteria, or bacterial biofilms. The chemistrode can be used for sampling on the surface of tissues for secreted chemicals, or cells that detach. When using the device the plug fluid can include reagents that stabilize the sample, such as anticoagulant, or it can contain reagents that help remove cells from the tissue. It can be used for chemical catalysis, for pattern-forming systems, to examine hormonal secretion, to examine viral infections, to detect DNA and RNA, to deliver or sample RNAi, to detect or deliver other signaling molecules, to set up in gradients of tissue, to study exocytosis, to study metabolic regulation of insulin, or to study the production of reactive oxygen species.

The chemistrode may be used for diagnostics and drug delivery. The advantages of the chemistrode, as opposed to devices with one or more tubes with single phase flow, include the ability to deliver pulses of chemicals in a time-controlled way, and the ability to provide feedback and delivery in the same system. For example, the chemistrode could be used to detect relevant levels of physiological markers, pass this information to a microprocessor, and dispense the required amount of drug. This kind of system could, for example, be used as an artificial pancreas. The chemistrode can add pulses of drugs to dose patients in a discrete way. For example, the device can be used as an implantable drug delivery device. Examples of implantable drug delivery devices and their applications are described in U.S. Pat. Nos. 6,551,838, 6,849,463 and 7,410,616 and U.S. patent application Ser. Nos. 11/927,092 and 11/927,156, all of which are hereby incorporated by reference herein in their entireties. The chemistrode can be used to add many different chemicals or to serially add mutually incompatible compounds that cannot be delivered through the same tube using single phase flow. Examples of mutually incompatible compounds include but are not limited to: activators and inhibitors (which would lead to incompatible actions); compounds that are incompatible chemically (such as acids and bases or reducing and oxidizing agents); and processes requiring incompatible conditions (such as different solvents or different pH). For many chemistrode applications the device can be designed to be swallowed, implanted, or applied locally to the surface of tissue. A component to initiate the flow may be incorporated in the device. Methods to initiate flow include, but are not limited to, positive or negative pressure, for example generated by a chemical or electrochemical reaction forming or consuming gas, electroosmotic forces, thermal expansion, phase transitions, and wicking. For example a plurality of liquid or solid substances may be brought into that together produce a gaseous product, thereby generating pressure. For example a solution of sulfuric acid and a carbonate salt may be used. Alternatively, a catalyst may be added to an area containing substances that do not react or only react slowly in the absence of the catalyst but which react more rapidly in the presence of the catalyst. One example is a mixture of sodium bicarbonate with a solid acid, for example tartaric acid, activated by addition of water, acting as a catalyst. A number of such mixtures capable of being activated by catalysts are used as baking powders. Alternatively, substances may be brought together such that a gaseous substance is consumed, thereby generating negative pressure and inducing motion of matter in a device. For example, sodium hydroxide and carbon dioxide will react in such a manner. Phase transitions may also be used to induce motion of matter in a device. In addition, wicking may be used. For example a first area may contain, or be composed of a material that absorbs matter in order to induce motion.

The chemistrode can also be used in situations where small volumes are critical: for example when the chemicals are very expensive or dangerous to handle. The chemistrode can be used in situations where one would want to avoid the sample inside the plugs touching the walls of the tubing. These situations could include collection/delivery of particles, cells, or viscous matter and other species that don't flow through tubes well. The chemistrode can be used for fast processes that require rapid control/addition. The chemistrode can be used for adding unstable intermediates or for highly unstable chemicals that can be generated in situ and delivered. A plug-formation device can be coupled upstream of the delivery channel for this application.

The chemistrode may be used for environmental monitoring, and/or delivering chemicals to the environment and at the same time recording the chemical response of the environment in plugs. The chemistrode may be used for microfabrication, drug discovery, research animal testing, manufacturing, and microbial isolation and discovery.

The chemistrode may also be used for the spatial imaging of enzymes. One can simply immobilize the enzymes on the surface (using methods such as stamping) at different concentrations (or using different enzymes) and image the surface with subsequent analysis. An array of chemistrodes may also be used, for example, a line of 5 or more devices to image the products. One could deliver 10 different enzymatic substrates in plugs a sequential array of ten plugs, and repeat the sequence n times, using 10×n plugs, and could then sample surfaces of arbitrary enzymatic complexity potentially in a cell or an embryo. The enzymatic substrates do not have to be labeled as long as one can use MALDI or FCS to detect them. This would enable one to create a spatial map of enzymatic activity. This could be done with patterned Lipid surfaces. If the activity of a membrane protein depends on the solution environment (pH, etc) one could deliver a sequence of 100 conditions to the surface, and see which gave the activity. One could do the same thing in solution.

In certain embodiments, the chemistrode may also be used to deliver protein aggregates to cultured neurons, other cells or parts of cells. First plugs can be used to generate aggregates in steady state at a fixed time point by flowing them a fixed distance. Then the chemistrode can be used to deliver well-defined aggregates to neurons and/or other cells (or even parts of cells). The chemistrode can then be used to pick up responses (in addition to doing optical imaging). One could then independently characterize what those aggregates do and could perform potential toxicity assays.

The chemistrode may be used to look at the timing of production of clotting factors, including on an unpatterned surface. The chemistrode can be used to look at absolute timing, and at the ratios of factors. For example, if blood coagulation factor Xa (FXa) is produced just as fast as a control, but thrombin takes a long time to be produced, the clotting problem would be determined to be in the lower part of the pathway.

The chemistrode can also be used for stimulating and recording responses from a substrate with high temporal and spatial resolution, as demonstrated using the chemistrode to record the secretion of insulin and zinc simultaneously from islets. A potential bottleneck of using the chemistrode for single cell assays includes the potential difficulty of aligning the chemistrode with a single cell and avoiding causing physical damage to a cell. Several methods for fixing cells and avoiding damage of cells can be integrated with the chemistrode: For example, (1) A cell can be located at the tip of a capillary tube by dispersing cells in a solution and injecting the solution into a capillary tube. When the cell reaches the desired position in the capillary tube, gelation of the solution is induced to fix the position of the cell. This approach assists the application of the chemistrode to single cell analysis and to 3D cell cultures in gels; (2) Single cells or bacteria can be captured in wells etched on the end of optical-fiber bundles, while being interrogated using the chemistrode. The optical fiber can allow real-time monitoring of cells under the chemistrode; (3) Electrodes can be integrated in the exchange region of the chemistrode to allow for electrical monitoring of electrochemically activity in the plugs.

In certain embodiments, the chemistrode can be applied to a cell that can release an enzyme or activate an enzyme (for example, thrombin, platelets, caspases, β-galactosidase enzymes, etc.). A first plug can be applied by the chemistrode to collect enzyme molecules. Optionally, a second plug with some form of stimulus (or, for example, a lysis buffer) can then be delivered. Optionally, a third plug can then collect a response. In certain embodiments, the numbers of molecules released can be measured by breaking up the plug collected from the cell into many sub-picoliter drops containing one molecule each.

The chemistrode can be used to study, for example, protease secretion from bacteria, fertilization (for example, proteases produced by embryos during implantation), cancer cells producing signaling factors or proteases during metastasis, viral proteases, cells and molecules involved in neural development, and PAR proteins.

The chemistrode can be used to deliver different drugs with time resolution, and even drugs that might react with each other when delivered in a single stream can be delivered. Highly unstable drugs can be generated and delivered in situ when a plug-formation device is coupled upstream of the delivery channel. The device can be swallowed, implanted, or applied locally to the surface of tissue. It can also be applied to the surface of tissues such as skin.

The chemistrode can be used for 3D printing and surface patterning, making microarrays, loading microwells, well plates or SlipChip devices. The chemicals to be applied to a surface are encapsulated in individual plugs and deposited on the surface one by one. For 3D printing, plugs are deposited one by one to make 3D features. The chemistrode can be applied to other processes where different chemicals need to be added in discrete volumes. For loading microwells, well plates, SlipChip devices, etc., the exchange region of the device can be placed in or above the microwell to be loaded, and flow is initiated to allow deposition of one or more plugs into the well, or to allow exchange of materials with the well.

In certain embodiments, a chemistrode can be used for drug discovery and high-throughput screening. In this application chemicals to be screened can be encapsulated in plugs. When plugs pass over a substrate, the response of the substrate is monitored in real time by techniques such as fluorescence microscopy, electrochemistry, etc., or recorded in plugs and analyzed later.

A chemistrode can be used for environmental monitoring. In this application plugs are formed from an environmental liquid or suspended in a plug fluid and either analyzed in real-time or stored and analyzed later.

A chemistrode can be used for microbial discovery and isolation. The chemistrode can be used for localized microsampling of microbial strains along with their respective environmental matrices and screening of wide array of growth conditions. The chemistrode can be used to isolate single cells, which can be useful for cells that are out-competed by other dominant species when mixed together. Confinement of single cells in plugs can also enhance the growth of cells. The localized sampling of microorganisms along with their native environmental matrices has been an important microbiological challenge. Most of the alternative current sampling methods obliterate the micro-environments during sampling and processing. In certain embodiments, a chemistrode can be use to collect micro-gram to nano-gram samples in confined volumes. An important advantage of such micro-sampling is that it can maintain inter-species associations (e.g. symbiosis), including, for example, natural growth inducing molecular signals. The chemistrode can be used for the cultivation of microorganisms that have not been cultivated so far using standard sampling and cultivation approaches. The device also enables sampling from heterogeneous environments.

Another microbiological application of the chemistrode is the use of multiple arrays for plug-based screening of growth conditions. Known cultivation methods are limited to relatively few growth conditions (for example, the type of growth substrate, pH, incubation temperature, gaseous requirements, etc.). With a chemistrode, a very small amount of sample can be screened for, for example, hundreds to thousands of growth parameters and it can be used for the cultivation of uncultured microorganisms. The plugs prepared with the chemistrode are usually surrounded by the carrier fluid and typically the aqueous contents do not touch the walls of the chemistrode. Also the chemistrode can be used for the rapid confinement of microbial samples collected from different sampling sites, along with local soil particles.

The chemistrode can also be used for 2D-surface characterization, and 3D sampling. The chemistrode can be coupled to mass spectrometry to characterize a surface. The chemistrode can be used in an imaging mode (such as in a spatially-dependent operation) to produce a 2D image of a surface using mass spectrometry. Known methods of surface analysis include applying a matrix directly to a surface. However, diffusion of the matrix and/or sample is a significant problem in such methods. Using a chemistrode coupled to robotics for x-y movement eliminates the sample diffusion problem. The device can also be used to sample off thin layer chromatography gels, other 1D, 2D and 3D separation media, and blotting media, microwells, well plates, SlipChips, etc. To sample microwells, the exchange region of a device is placed in the microwell to generate one or more plugs of the sample in the well. The device is then moved to the next well for sampling. Optionally an array of devices can be used to sample multiple locations simultaneously. Optionally the flow can be stopped when the device is moved from one well to the other. Optionally a computer program may be used to control the flow and the movement of the sampling device. The device can be coupled to additional analytical chemistry techniques to provide for surface information, including but not limited to spectroscopy, chromatography, titrimetry, potentiometry and voltammetry.

The chemistrode can be used for all applications of the plug systems known in the art. Since the device can contain a plug formation component, all the applications of the plug-based system can be realized here, including stochastic confinement of cells and/or particles from a suspension.

While the present disclosure has been described with reference to certain embodiments, other features may be included without departing from the spirit and scope of the present invention. It is therefore intended that the foregoing detailed description be regarded as illustrative rather than limiting, and that it be understood that it is the following claims, including all equivalents, that are intended to define the spirit and scope of this invention.

The invention claimed is:

1. A method for sampling and/or introducing a matter to an environment, comprising:
   introducing a first array of plugs through a first microchannel of a device into an exchange region of the device, the exchange region being exposed to a living environment and in which mass transport of a matter between the living environment and the plug fluid of at least one plug in the first array of plugs occurs such that a second array of plugs is formed; wherein the exchange region is in fluid communication with the first microchannel; and directing the second array of plugs into a second microchannel downstream of and in fluid communication with the exchange region.

2. The method of claim 1, further comprising analyzing the contents of at least one plug in the second array of plugs.

3. The method of claim 1, further comprising introducing the matter to at least one plug in the first array of plugs in the first microchannel.

4. A method comprising:
introducing a first array of plugs through a first microchannel of a device into an exchange region of the device, the exchange region being exposed to an environment and in which mass transport of a matter between the environment and the plug fluid of at least one plug in the first array of plugs occurs such that a second array of plugs is formed; wherein the exchange region is in fluid communication with the first microchannel; and
directing the second array of plugs into a second microchannel downstream of and in fluid communication with the exchange region,
wherein the exchange region comprises a membrane disposed between the first array of plugs and the environment, the membrane allowing selective mass transport of the matter between the environment and the plug fluid of at least one plug in the first array of plugs.

5. The method of claim 4, wherein the environment is the interior of a cell, the exterior of a cell, an intracellular space between cells, a tissue culture, a living organism, a community of organisms, a body of water, a soil sample or a gas.

6. A method for sampling and/or introducing a matter to an environment, comprising:
introducing a first array of plugs through a first microchannel of a device into an exchange region of the device, the exchange region being exposed to an environment and in which mass transport of a matter between the environment and at least one plug in the first array of plugs occurs such that at least one biological cell contained within the environment is transported into the plug fluid of at least one plug from the first array of plugs so that a second array of plugs forms,
wherein the exchange region is in fluid communication with the first microchannel; and
analyzing the contents of at least one plug in the second array of plugs after it passes the exchange region.

7. The method of claim 6, wherein the environment comprises biological material.

8. The method of claim 7, wherein the biological material is part of a living organism.

9. The method of claim 7, wherein the biological material is in the circulatory system or the brain.

10. The method of claim 6, wherein the size of the first microchannel, the size of the plugs, the speed of movement of the array of plugs and the size and/or shape of the exchange region in which mass transport between the environment and at least one plug in the first array of plugs occurs are such that the at least one biological cell contained within the environment is transported into the plug fluid of at least one plug from the first array of plugs when the second array of plugs is formed.

11. The method of claim 6, further comprising:
providing a stimulus to the environment, wherein the stimulus is adjusted as a function of a result of the analysis of the contents of at least one plug in the second array of plugs.

12. The method of claim 7, further comprising:
providing a stimulus to the living organism, wherein the stimulus is adjusted as a function of a result of the analysis of the contents of at least one plug in the second array of plugs.

13. The method of claim 12, wherein the stimulus is at least one of a visual, tactile, auditory, olfactory or gustatory stimulus.

14. The method of claim 6, wherein the at least one plug in the first array of plugs comprises the matter, which is introduced to the environment in the exchange region.

15. The method of claim 14, further comprising:
adjusting at least one of the rate, amount and composition of the introduced matter based on a result of the analysis.

16. The method of claim 14, further comprising:
varying the amount, varying the composition, or varying both the composition and amount of the introduced matter across the array of plugs.

17. A method for sampling an aqueous environment, comprising:
introducing a fluid through a first microchannel of a device, wherein the fluid is immiscible with water, into an exchange region of the device, the exchange region being exposed to an aqueous environment and in which mass transport of a matter between the aqueous environment and the fluid occurs such that an array of plugs is formed in the exchange region upon the mass transport of the matter between the aqueous environment and the fluid, the exchange region in fluid communication with the first microchannel;
directing the array of plugs into a second microchannel downstream of and in fluid communication with the exchange region; and
storing, analyzing or both storing and analyzing the contents of at least one of the plugs.

18. The method of claim 17, wherein the fluid is a fluorinated oil.

19. The method of claim 17, wherein the exchange region is a portion of a curved third microchannel that connects the first and second microchannels.

20. The method of claim 17, wherein the exchange region is along the outside of a bent section of a third microchannel that connects the first and second microchannels.

21. The method of claim 17, further comprising:
introducing an aqueous stream through a third microchannel, in fluid communication with the exchange region, towards the exchange region such that at least a portion of the aqueous stream is incorporated into the array of plugs that are formed in the exchange region.

22. A method for introducing a matter to an environment, comprising:
introducing an array of plugs comprising a carrier fluid and at least one plug, wherein the at least one plug comprises a plug fluid and a matter to be introduced, through a first microchannel of a device into an exchange region of the device, the exchange region being exposed to an environment and in which mass transport of the matter between the environment and the at least one plug in the array of plugs occurs wherein the exchange region is in fluid communication with the first microchannel;
directing the carrier fluid into a second microchannel downstream of and in fluid communication with the exchange region, such that the second microchannel is substantially free of plugs; and directing substantially all of the plug fluid of the array of plugs into the environment.

23. The method of claim 22, wherein the interior surface of the second microchannel is preferentially wetted by the carrier fluid relative to the plug fluid.

* * * * *

UNITED STATES PATENT AND TRADEMARK OFFICE
CERTIFICATE OF CORRECTION

PATENT NO. : 8,622,987 B2  Page 1 of 1
APPLICATION NO. : 12/737058
DATED : January 7, 2014
INVENTOR(S) : Ismagilov et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 237 days.

Signed and Sealed this
Twenty-second Day of September, 2015

Michelle K. Lee
*Director of the United States Patent and Trademark Office*